(12) United States Patent
Wei et al.

(10) Patent No.: US 9,802,972 B2
(45) Date of Patent: Oct. 31, 2017

(54) RUTHENIUM- OR OSMIUM-BASED COMPLEX CATALYSTS

(71) Applicant: LANXESS Deutschland GmbH, Cologne (DE)

(72) Inventors: Zhenli Wei, Shanghai (CN); Qingchun Liu, Shandong (CN)

(73) Assignee: ARLANXEO DEUTSCHLAND GMBH, Dormagen (DE)

( * ) Notice: Subject to any disclaimer, the term of this patent is extended or adjusted under 35 U.S.C. 154(b) by 0 days.

(21) Appl. No.: 14/896,412

(22) PCT Filed: Jun. 6, 2014

(86) PCT No.: PCT/EP2014/061823
§ 371 (c)(1),
(2) Date: Dec. 7, 2015

(87) PCT Pub. No.: WO2014/198658
PCT Pub. Date: Dec. 18, 2014

(65) Prior Publication Data
US 2016/0122376 A1    May 5, 2016

(30) Foreign Application Priority Data
Jun. 9, 2013  (WO) ................ PCT/CN2013/077107

(51) Int. Cl.
*C07C 19/00* (2006.01)
*C07F 15/00* (2006.01)
(Continued)

(52) U.S. Cl.
CPC ....... *C07F 15/0046* (2013.01); *B01J 31/2217* (2013.01); *B01J 31/2243* (2013.01);
(Continued)

(58) Field of Classification Search
CPC .. C01G 55/008; C07F 15/002; C07F 15/0046; C08C 19/02
(Continued)

(56) References Cited

U.S. PATENT DOCUMENTS

| | | |
|---|---|---|
| 5,021,469 A | 6/1991 | Langerbeins et al. |
| 5,087,676 A | 2/1992 | Heider et al. |

(Continued)

FOREIGN PATENT DOCUMENTS

| | | | |
|---|---|---|---|
| EP | 2151445 A | | 8/2008 |
| JP | 2002-030057 | * | 1/2002 |

(Continued)

OTHER PUBLICATIONS

The Handbook of Homogeneous Hydrogenation, 2007, vol. 1, pp. 45-70 (Edited by De Vries, Johannes G.; Elsevier, Cornelis J).
(Continued)

*Primary Examiner* — Robert C Boyle

(57) ABSTRACT

The present invention provides novel ruthenium or osmium based complex structures with a unique combination of ligands comprising a Schiff-base type ligand, a N-heterocyclic carbene ligand and a CO ligand which can be prepared according to two different routes involving easily accessible starting materials and which represent excellent catalysts for
(Continued)

hydrogenating unsaturated compounds, oligomers and polymers, in particular at unforeseeably low temperatures.

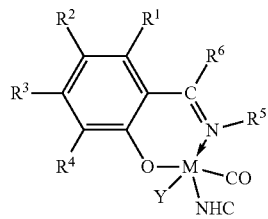

(I)

30 Claims, 3 Drawing Sheets

(51) Int. Cl.
  *B01J 31/22* (2006.01)
  *C08C 19/02* (2006.01)
  *C08L 15/00* (2006.01)
  *C07C 5/03* (2006.01)
  *C08F 236/12* (2006.01)

(52) U.S. Cl.
  CPC ....... *B01J 31/2273* (2013.01); *B01J 31/2278* (2013.01); *C07C 5/03* (2013.01); *C08C 19/02* (2013.01); *C08F 236/12* (2013.01); *C08L 15/005* (2013.01); *B01J 2231/645* (2013.01); *B01J 2531/821* (2013.01); *B01J 2531/825* (2013.01); *C07C 2531/22* (2013.01)

(58) Field of Classification Search
  USPC ........................................................ 525/326
  See application file for complete search history.

(56) References Cited

U.S. PATENT DOCUMENTS

| | | | |
|---|---|---|---|
| 5,340,858 A | 8/1994 | Bauer et al. | |
| 5,414,193 A | 5/1995 | Taylor et al. | |
| 5,436,289 A | 7/1995 | Aydin et al. | |
| 5,496,882 A | 3/1996 | Aydin et al. | |
| 5,498,655 A | 3/1996 | Aydin et al. | |
| 5,624,992 A | 4/1997 | Aydin et al. | |
| 5,708,077 A | 1/1998 | Nolken et al. | |
| 5,756,574 A | 5/1998 | Baumstark et al. | |
| 5,977,393 A * | 11/1999 | Grubbs | C07F 15/0046 264/171.23 |
| 5,994,457 A | 11/1999 | Stanger et al. | |
| 6,635,768 B1 | 10/2003 | Hermann et al. | |
| 8,877,936 B2 | 11/2014 | Grubbs et al. | |
| 2007/0185343 A1 | 8/2007 | Verpoort et al. | |
| 2011/0124868 A1 | 5/2011 | Grubbs et al. | |
| 2011/0137043 A1* | 6/2011 | Drozdzak | C07F 15/0046 548/103 |
| 2015/0057450 A1 | 2/2015 | Jeschko et al. | |

FOREIGN PATENT DOCUMENTS

| | | |
|---|---|---|
| JP | 2002030006 A2 | 1/2002 |
| JP | 2002030057 A | 1/2002 |
| WO | 2014198658 A1 | 6/2014 |

OTHER PUBLICATIONS

Chang, S., "Synthesis and Characterization of New Ruthenium-Based Olefin Metathesis Catalysts Coordinated with Bidentate Schiff-Base Ligands", Organometallics, 1998, 17(16), pp. 3460-3465.
Vougioukalakis, G. C. "Ruthenium-Based Heterocyclic Carbene-Coordinated Olefin Metathesis Catalysts", Chem. Rev., 2010, 110 (3), pp. 1746-1787.
Opstal, T. "Synthesis of Highly Active Ruthenium Indenylidene Complexes for Atom-Transfer Radical Polymerization and Ring-Opening-Methathesis Polymerization", Angew. Chem. Int. Ed. 2003, 42(25), pp. 2876-2879.
Monsaert, S. "A Highly Controllable Latent Ruthenium Schiff Base Olefin Metathesis Catalyst: Catalyst Activiation and Mechanistic Studies", Journal of Polymer Science: Part A: Polymer Chemistry, vol. 48, pp. 302-310 (2010).
Ledoux, N. "Exploring new synthetic strategies in the development of a chemically activiated Ru-based olefin metathesis catalyst", Dalton Translation , 2007, pp. 5201-5210.
Binder, J.B. "Salicylaldimine Ruthenium Alkylidene Complexes: Metathesis Catalysts Tuned for Protic Solvents", Adv. Synth. Catal., 2007, Department of Chemistry, University of Wisconsin-Madison, Madison WI, 349, pp. 395-404.
Occhipinti, G. "Green and Efficient Synthesis of Bidentte Schiff Base Ru Catalysts for Olefin Metathesis", Journal of Organic Chemistry 2007, 72, pp. 3561-3564.
Balasubramanian, K.P., "Ruthenium(II) complexes containing triphenylphosphine/triphenylarsine and bidentate Schiff bases derived from 2-hydroxy-1-naphthaldehyde and primary amines", Transition Metal Chemistry 2004, 29, pp. 644-648.
Wilton-Ely, J. "Ruthenium hydride and vinyl complexes supported by nitrogen-oxygen mixed-donor ligands", Inorganica Chimica Acta 358, 2005, pp. 3218-3226.
Lee, J.P. "Six-, Five-,and Four Coordinate Ruthenium(II) Hydride Complexes Supported by N-Heterocyclic Carbene Ligands: Synthesis, Characterization, Fundamental Reactivity, and Catalytic Hydrogenation of Olefins, Aldehydes, and Ketones", Organometallics, 28, 2009, pp. 1758-1775.
International Search Report from co-pending Application PCT/EP2014/061823 dated Aug. 11, 2014,2 pages.
International Search Report from co-pending Application PCT/CN2013/077107 dated Mar. 13, 2014, 3 pages.
Methods of Organic Chemistry, Houben-Weyl, vol. XIV/1, Macromolecular Materials, Georg Thieme Verlag, Stuttgart, 1961, pp. 191-208.
Ullmann's Encyclopedia of Industrial Chemistry, Plastics, Properties and Testing to Polyvinyl Compounds, 5th, Completely Revised Edition, vol. A21, VCH Verlagsgesellschaft mbH, D-6940 Weinheim (Fed. Rep. of Germany), 1992 , pp. 373-393.

* cited by examiner

Figure 1: RDB depending on hydrogenation time for Comparative Examples 1 and 2 and Examples 3 to 8
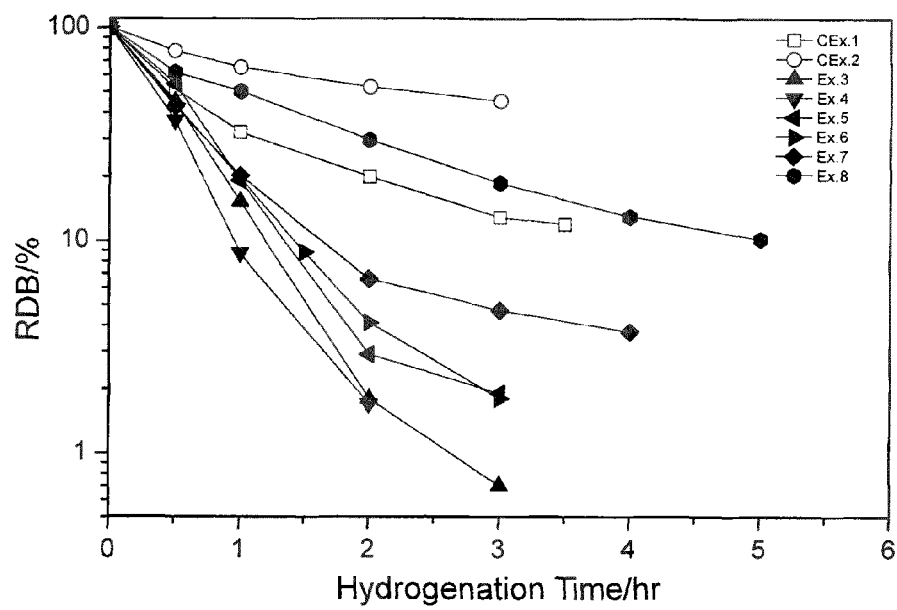
Figure 2: RDB depending on hydrogenation time for Examples 4, and 9 to 11
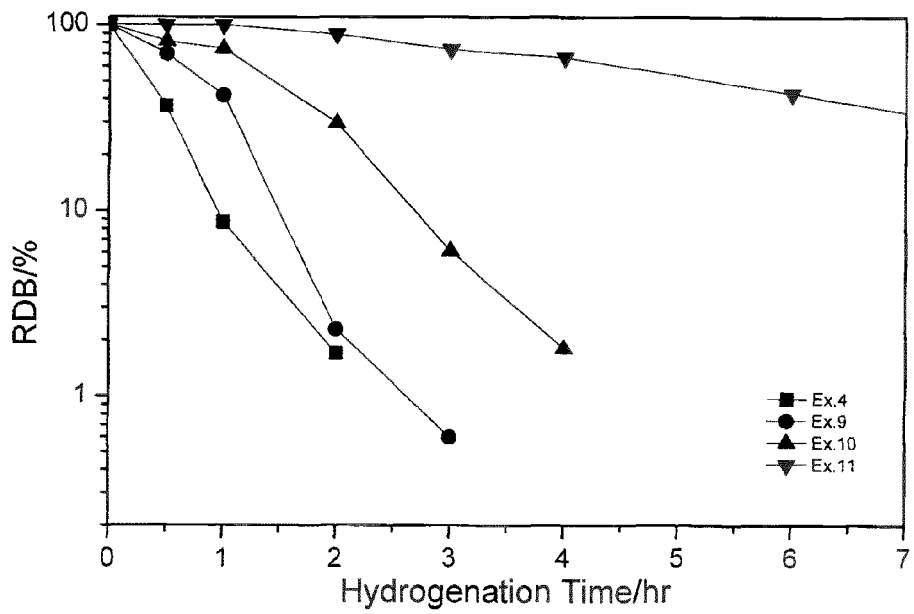

Figure 3: RDB depending on hydrogenation time for Examples 4 and 12
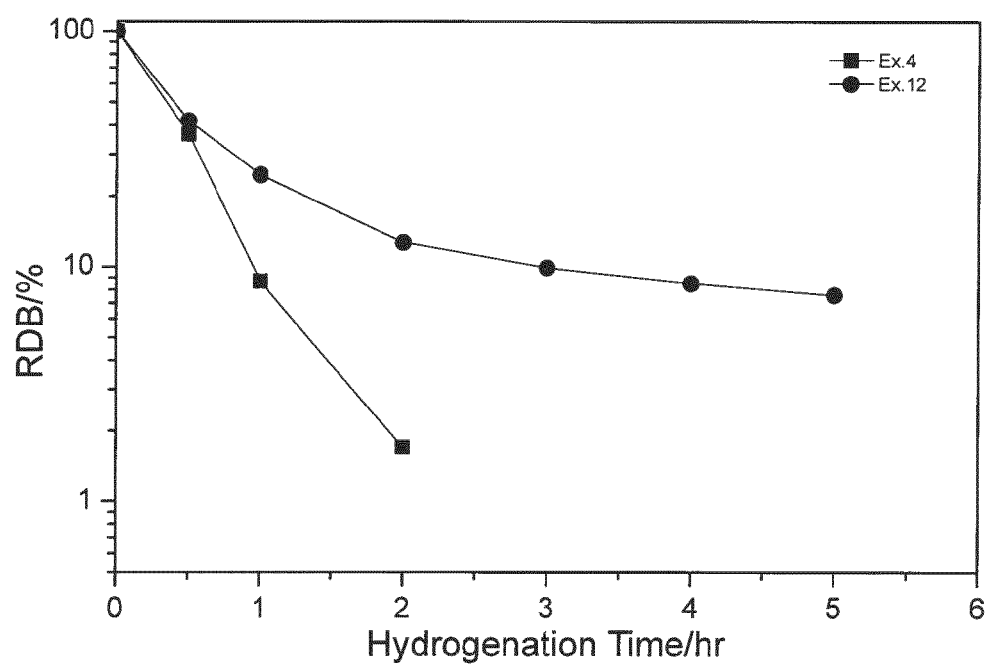

Figure 4: Structure of complex (Ia)-SIMes determined by single crystal XRD analysis
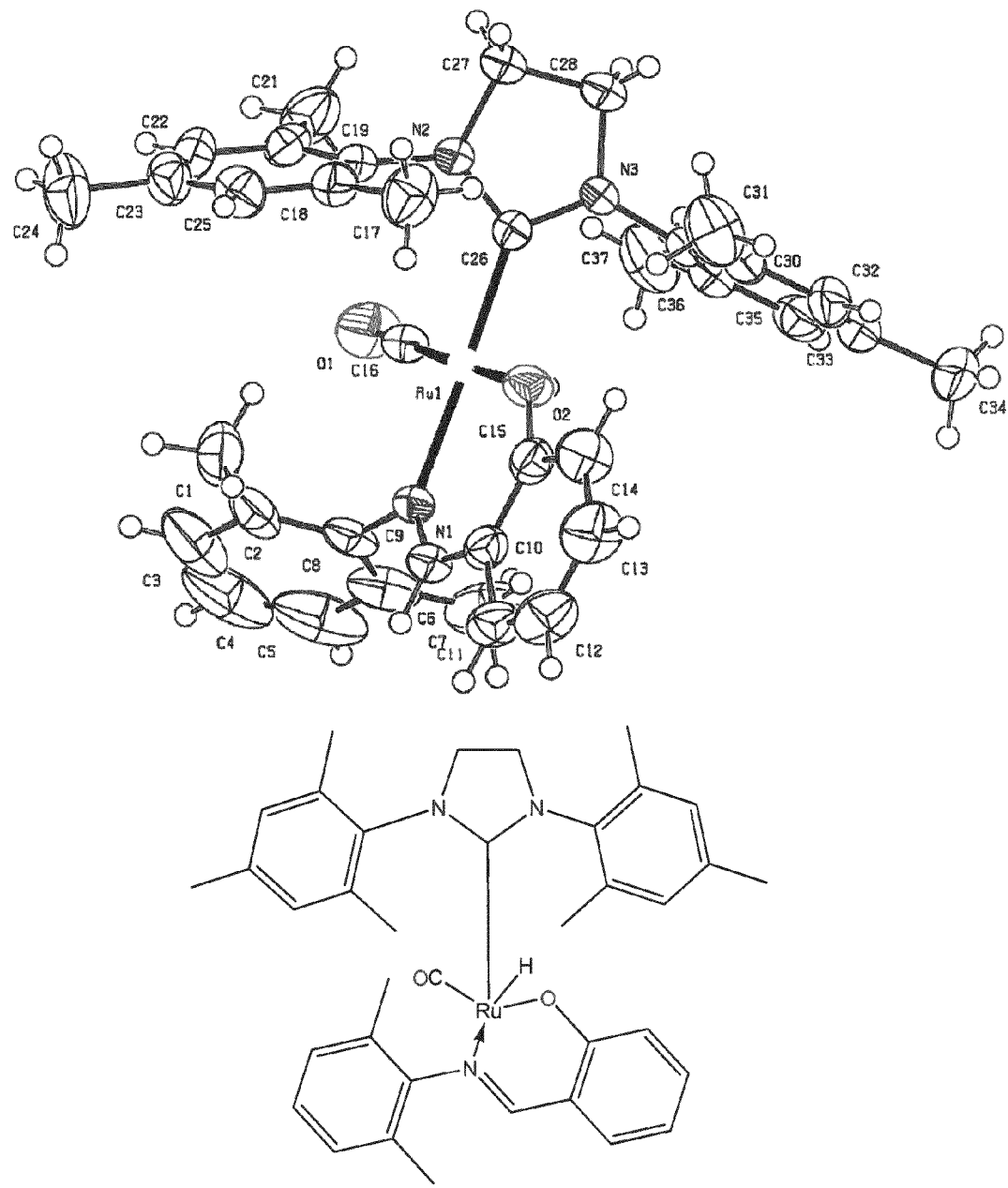

RUTHENIUM- OR OSMIUM-BASED COMPLEX CATALYSTS

FIELD OF THE INVENTION

The present invention relates to ruthenium and osmium based complex structures, to the synthesis thereof and the use as catalysts for hydrogenating unsaturated compounds.

BACKGROUND OF THE INVENTION

Ruthenium or Osmium based catalysts already play an important role in the homogeneous hydrogenation reactions of various substrates for many years as summarized in the Handbook of Homogeneous Hydrogenation, 2007, Volume 1, Pages 45-70 (Edited by De Vries, Johannes G.; Elsevier, Cornelis J).

In WO99/26949A1 and Organometallics, 1998, 17(16), 3460 ruthenium and osmium based complex catalysts have been disclosed which contain bidentate Schiff-Base ligands. It is reported that such complex catalysts are suited for olefin metathesis. It further on described that these ruthenium or osmium based Schiff Base complexes are highly stable to air, moisture and temperature and even exhibit catalytic activity in polar protic solvents. Said (O, N) bidentate Schiff base ligands were recognized as especially feasible for fine-tuning of ligand parameters since their steric and electronic environment can be tailored by the proper choice of the starting materials, i.e. the amine and salicyl aldehyde type. The ruthenium based complexes can be prepared by the treatment of $RuCl_2(=CHPh)(PCy_3)_2$ (3), the so-called Grubbs (I) catalyst, with a variety of Schiff-base ligands as thallium salts as shown in the following Scheme in which the compound numbering given below the formulae is the same as used in Organometallics, 1998, 17(16), 3460.

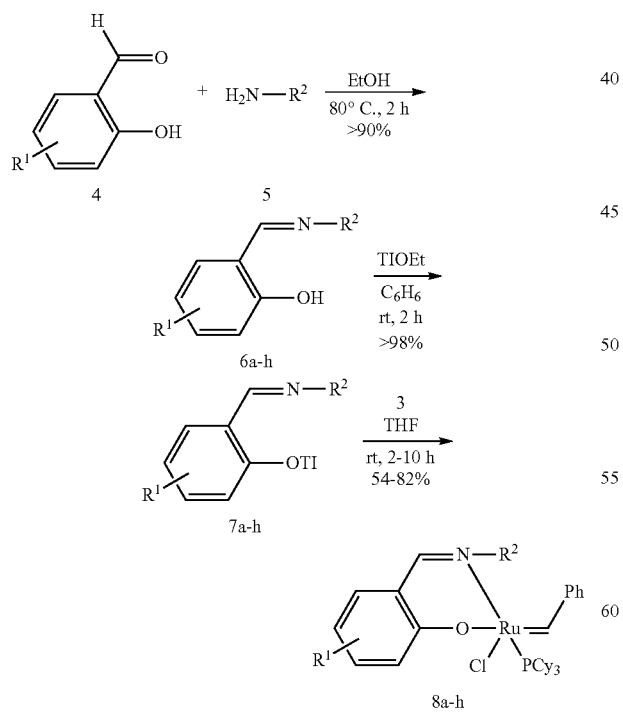

wherein $R^1$ and $R^2$ have the following meanings in compounds 8a-h:

8a $R^1$=H, $R^2$=2,6-i-$PrC_6H_3$
8b $R^1$=4-$NO_2$, $R^2$=2,6-i-$PrC_6H_3$
8c $R^1$=4-$NO_2$, $R^2$=2,6-Me-4-$MeOC_6H_2$
8d $R^1$=4-$NO_2$, $R^2$=2,6-Me-4-$BrOC_6H_2$
8e $R^1$=4-$NO_2$, $R^2$=2,6-Cl-4-$CF_3C_6H_2$
8f $R^1$=6-Me-4-$NO_2$, $R^2$=2,6-i-$PrC_6H_3$
8g $R^1$=4-$NO_2$, $R^2$=2,6-i-Pr-4-$NO_2$—$C_6H_3$
8h $R^1$=4-$NO_2$,

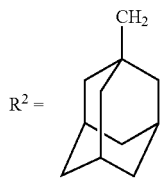

However, at metathesis temperatures around room temperature these ruthenium based Schiff Base complexes have a lower activity compared to Grubbs (I) catalyst which is $RuCl_2(=CHPh)(PCy_3)_2$, because they are highly thermally stable under standard catalytic reaction conditions. They only show a higher activity in ring-closing metathesis (RCM) reactions when these are performed at elevated temperatures as e.g. 70° C.

Chem. Rev., 2010, 110(3), 1746-1787 encompasses a review by G. C. Vougioukalakis and R. Grubbs that Schiff base N,O-bidentate ligands can be also introduced into NHC ligand containing Ru-based complexes (with "NHC" standing for a N-heterocyclic carbene ligand) and that the resulting complexes can act as catalysts for atom transfer radical polymerization (ATRP), ring-opening metathesis polymerization (ROMP), ring-closing metathesis (RCM), olefin isomerisation, enol ester synthesis and Kharasch addition. The Ru-based NHC-Schiff base metathesis catalysts disclosed have for example the following structures wherein the numberings given below the formulae are the same as used in Chem. Rev., 2010, 110(3), 1746-1787.

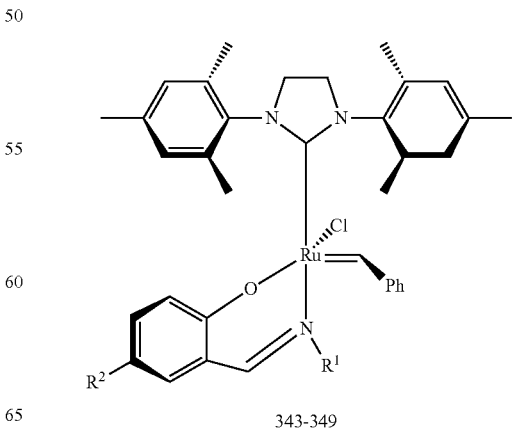

343-349

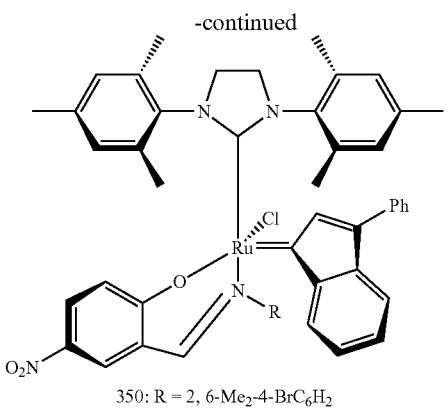

350: R = 2, 6-Me$_2$-4-BrC$_6$H$_2$ wherein R$^1$ and R$^2$ have the following meanings in compounds 343 to 349:
343 R$^1$=CH$_3$, R$^2$=H
344 R$^1$=CH$_3$, R$^2$=NO$_2$
345 R$^1$=2,6-(CH$_3$)$_2$-4-BrC$_6$H$_2$, R$^2$=H
346 R$^1$=2,6-(CH$_3$)$_2$-4-BrC$_6$H$_2$, R$^2$=NO$_2$
347 R$^1$=2,6-i-Pr$_2$-C$_6$H$_3$; R$^2$=H
348 R$^1$=2,6-i-Pr$_2$-C$_6$H$_3$; R$^2$=NO$_2$
349 R$^1$=2,4,6-(CH$_3$)$_3$—C$_6$H$_2$, R$^2$=H The catalysts of the following formulae are commercially available from Umicore as catalysts "M41" and "M42" and are recommended for metathesis reactions:

M41

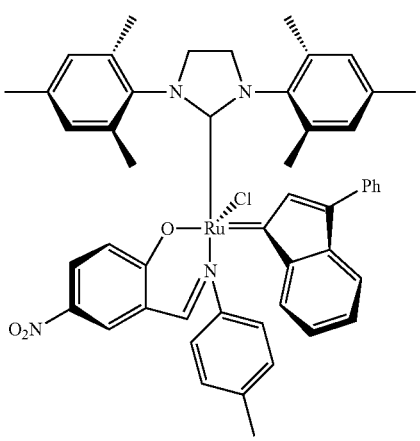

M42

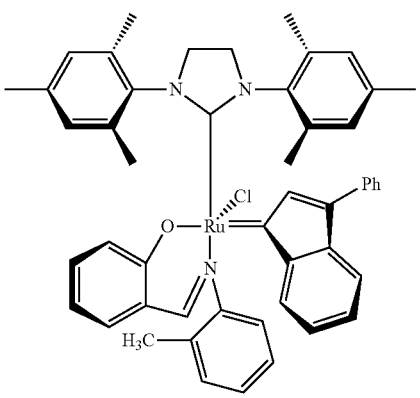

In Angewandte Chemie International Edition 2003, 42(25), 2876 T. Opstal and F. Verpoort have disclosed that the two donor atoms of Schiff base ligands in ruthenium based complexes have opposing natures: the phenolate oxygen atom is a hard donor and known to stabilize the higher oxidation states of ruthenium, whereas the imine nitrogen atom is in comparison soft and a stabilizer of the lower oxidation states. It was recognized that combining an N-heterocyclic carbene ligand carrying mesitylene groups as substituents of the two N atoms in the ligand with a bidentate Schiff base ligand in the same compound should lead to superior performance, because
1) the strong electron-donating ability of the imidazol-2-ylidene-type ligand, i.e. the N-heterocyclic carbene ligand, can facilitate the decoordination of one side of the bidentate ligand plus it can stabilize the generated intermediate;
2) the bulky mesitylene groups protect the second carbene species in the complex and prevent bimolecular decomposition; and
3) with a phosphane-free catalyst, P—C decomposition reactions are avoided.

However, it is further reported that besides the increased stability, the association of both, the bidentate Schiff base ligands and NHC ligands into Ru complexes also causes rather low catalytic activity at lower temperature. To achieve an activation of this type of "latent" Ru—NHC-Schiff Base catalysts, specific protocols, e.g. heating or introduction of acidic co-catalysts (HCl, BF$_3$, SiCl$_4$, HSiCl$_3$ etc.) are needed as e.g. reported in J. Polym. Sci. A Polym. Chem., 2010, 48(2), 302, as well as Dalton Trans, 2007, 44, 5201.

In Adv. Synth. Catal., 2007, 349(3), 395-404 it is disclosed that catalysts bearing both bidentate salicylaldimine ligands and NHC ligands represent robust olefin metathesis catalysts and test data has been provided for successful ring-closing metathesis of dienes and enynes in methanol and methanol/water mixtures under air. Examples of the investigated catalysts are shown in the following wherein the compound numberings given below the formulae are the same as used in Adv. Synth. Catal., 2007, 349(3), 395-404. The synthetic routes again employ the Schiff base ligands as highly toxic Tl(I) salts.

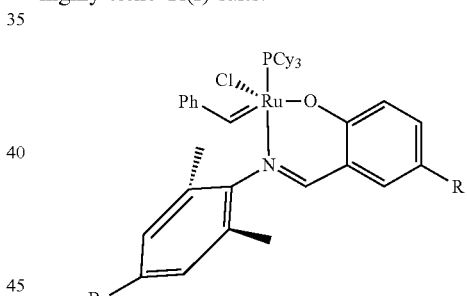

6a R = H
b R = NO$_2$
c R = N(CH$_3$)$_3$ + Cl$^-$

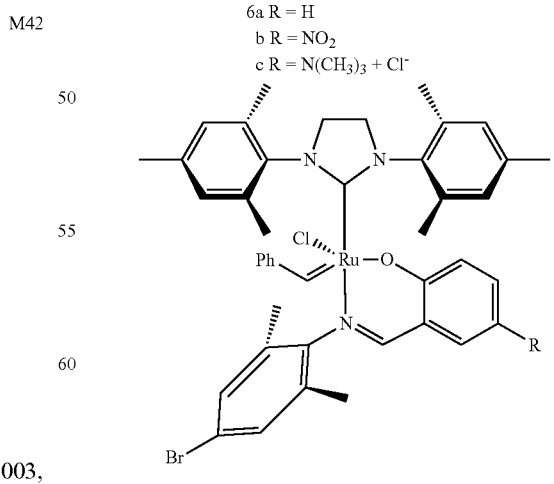

7a R = H
b R = NO$_2$
c R = N(CH$_3$)$_3$ + Cl$^-$

In Journal of Organic Chemistry 2007, 72, 3561 a Tl salt free and efficient synthesis of bidentate Schiff Base ligand containing ruthenium based complex catalysts for olefin metathesis is described. The new synthesis involves a two-step, quasi-one-pot approach and Ag(I) carbonate as base as shown in the following scheme wherein $R^1$ and $R^2$ may different meanings as disclosed in Journal of Organic Chemistry 2007, 72, 3561.

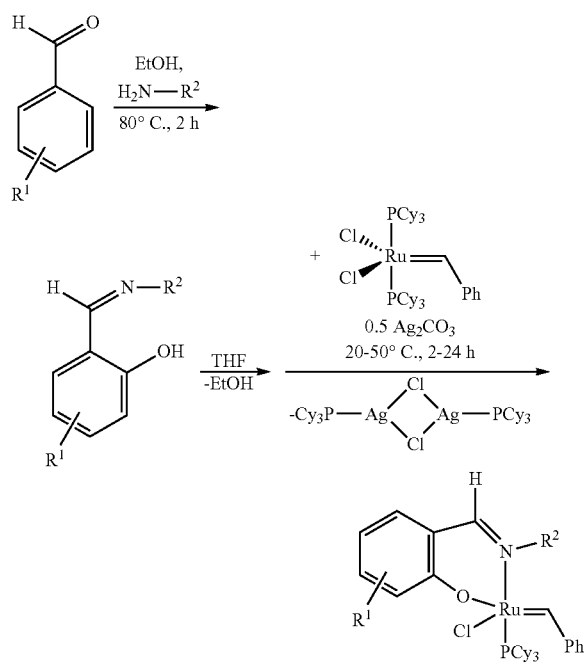

Although different Ruthenium based complex catalysts containing a NHC-ligand and a Schiff base type ligand have been reported in the prior art so far, they all have one common structural feature: besides the NHC ligands and Schiff base ligands, they all additionally contain a Ru-alkylidene structure [Ru=C—]. So far these Ru-based NHC-Schiff base catalysts are mainly disclosed as catalysts for atom transfer radical polymerization (ATRP), ring-opening metathesis polymerization (ROMP), ring-closing metathesis (RCM), olefin isomerisation, enol ester synthesis and Kharasch addition.

In JP 2002/030057A new ruthenium based complexes having a Schiff base ligand as shown below were synthesized and isolated.

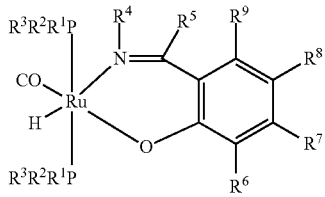

These complexes have been reported as being capable of exhibiting a higher catalytic activity for partial hydrogenation of a cyclic polyene such as cyclododecatriene to cyclododecene than that of a conventionally known catalyst system without using an additive which is indispensable to conventional ruthenium complex catalyst systems. JP 2002/030057A does not contain any disclosure or teaching whether or not such catalysts are suited and active for the hydrogenation of other types of compounds or polymers with high conversion rates and if yes under which conditions and with which activity.

In Transition Metal Chemistry 2004, 29, 644-648, an efficient method for introducing a bidentate Schiff base ligand into Ru complexes is described which yields new hexa-coordinated Schiff base complexes of the type [RuCl(CO)(EPh$_3$)(B)(L)] with E being P or As, B being PPh$_3$ or AsPh$_3$ or pyridin or piperidine and L being the anion of the Schiff bases derived from 2-hydroxy-1-naphthaldehyde and aniline, 4-chloroaniline or 2-methylaniline, respectively. This synthesis route operates in the absence of a metal catalyst mandatory pursuant to a number of other prior art references. The antibacterial activity of these complexes was investigated, but no catalytic properties were investigated or mentioned. The preparation process disclosed is shown in the following for E representing phosphorus, and B as well as L both being PPh$_3$.

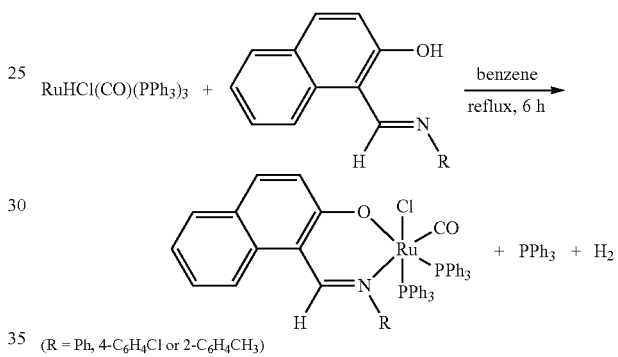

(R = Ph, 4-C$_6$H$_4$Cl or 2-C$_6$H$_4$CH$_3$)

In Inorganica Chimica Acta 358, 2005, 3218-26, a complex RuHCl(CO)(PPh$_3$)$_3$ is converted with 2,1,3-benzothiadiazole ("BTD") to prepare the complex RuHCl(CO)(PPh$_3$)$_2$(BTD). A Schiff base is then added to the complex RuHCl(CO)(PPh$_3$)$_2$(BTD) to remove the BTD ligand in order to introduce the Schiff-base ligand to the Ru/Os metal center as shown in the following scheme. When the complex RuHCl(CO)(PPh$_3$)$_2$(BTD) is reacted with the Schiff-base ligand, the obtained Ru Schiff-based complex is generated in microcrystalline form which can be easily (re)crystallized from the reaction system with very good purity.

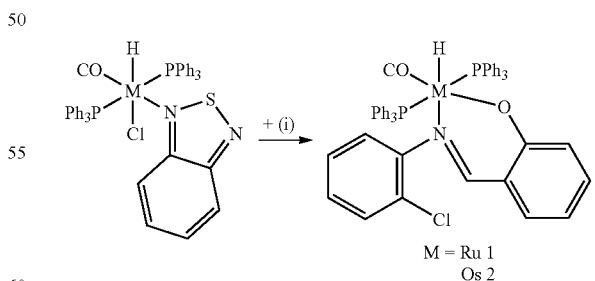

M = Ru 1
Os 2 wherein (i) means

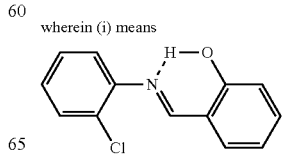

As the hydrogenation of compounds is of high importance it was the object of the present invention to provide access to novel ruthenium or osmium based complexes which are excellent hydrogenation catalysts on the one hand and which show a high stability in air or water on the other hand. In particular such complexes should dispose of a high hydrogenation activity for large-scale industrial use at ambient reaction conditions. Preferably such novel complexes should exhibit a high hydrogenation activity even at low reaction temperatures. With regard to the hydrogenation of nitrile rubber the current industrial processes often use expensive Rh-based catalyst systems like Wilkinson's catalyst together with $PPh_3$ as co-catalyst. After hydrogenation, extra time and costs must be spent to remove and recycle the expensive Rh-based catalyst. It would be desirable to find a catalyst disposing of such a high activity that no co-catalyst needs to be used anymore on the one hand and recovery and recycling of the catalyst would no longer be necessary on the other hand. This would reduce catalyst costs as well as process costs substantially. Compared to hydrogenated polymers as obtained nowadays with known catalysts it is important that the hydrogenated polymers to be obtained by using any new complex catalyst must not show any changes in polymer properties and the polymer's vulcanization behaviour as this has been unfortunately observed for other catalysts.

This object has now been solved by providing novel ruthenium or osmium based complex catalysts containing on the one hand a Schiff-base type ligand and on the other hand an N-heterocyclic carbene ("NHC") ligand, but no Ru- or Os-alkylidene structure.

SUMMARY OF THE INVENTION

The invention relates to novel complexes having the general formula (I)

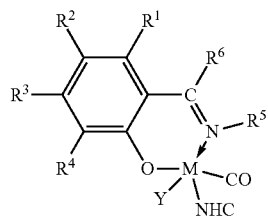

wherein

M is ruthenium or osmium

Y represents H, F, Cl, Br, I, $CF_3$, pyridine, —$OC_6H_5$, $CF_3COO$—, $CH_3SO_3$—, or $BF_4$ $R^1$, $R^2$, $R^3$, and $R^4$ are identical or different and represent H; $NO_2$; $CF_3$; halogen, preferably F, Cl, Br, or I; or straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl; or substituted or unsubstituted $C_3$-$C_{10}$-cycloalkyl, preferably $C_5$-$C_8$-cycloalkyl, more preferably cyclopentyl, cyclohexyl or cycloheptyl; or substituted or unsubstituted $C_6$-$C_{14}$-aryl, preferably $C_6$-$C_{10}$-aryl, more preferably phenyl, is either unsubstituted or contains 1, 2, 3, 4 or 5 substituents; or $OR^7$, $OC(=O)R^7$, $CO(=O)R^7$, $SO_3R^7$, $SO_3N(R^7)_2$ or $SO_3Na$ wherein $R^7$ represents H, straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl; or $(N(R^8)_3)^+X^-$ wherein X is halide, preferably chloride, and $R^8$ are identical or different and represent H; straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl; substituted or unsubstituted $C_6$-$C_{14}$-aryl, preferably $C_6$-$C_{10}$-aryl, more preferably phenyl, which aryl group, more preferably phenyl, is either unsubstituted or contains 1, 2, 3, 4 or 5 identical or different substituents; most preferably $N(CH_3)(C_2H_5)_2{}^+Cl^-$, $N(C_2H_5)_2H^+Cl^-$, $NH_3{}^+Cl^-$, $NH(CH_3)_2{}^+Cl^-$, or $N(CH_3)_3{}^+Cl^-$;

tris ($C_1$-$C_6$-alkoxy)silyl-$C_1$-$C_6$-alkyl, tris ($C_6$-$C_{14}$-aryloxy)silyl-$C_1$-$C_6$-alkyl, or tris($C_3$-$C_{10}$-cycloalkoxy)silyl-$C_1$-$C_6$-alkyl, preferably trisethoxysilyl-n-propyl;

$R^5$ represents H; or straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl; or substituted or unsubstituted $C_3$-$C_{10}$-cycloalkyl, preferably $C_5$-$C_8$-cycloalkyl, more preferably cyclopentyl, cyclohexyl or cycloheptyl; or substituted or unsubstituted $C_6$-$C_{14}$-aryl, preferably $C_6$-$C_{10}$-aryl, more preferably phenyl, which aryl group, preferably phenyl, is either unsubstituted or contains 1, 2, 3, 4 or 5 identical or different substituents, even more preferably 1, 2 or 3 identical or different substituents which are located in the o- and/or p-positions; or $R^6$ represents H, or straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl; or substituted or unsubstituted $C_3$-$C_{10}$-cycloalkyl, preferably $C_5$-$C_8$-cycloalkyl, more preferably cyclopentyl, cyclohexyl or cycloheptyl; or substituted or unsubstituted $C_6$-$C_{14}$-aryl, preferably $C_6$-$C_{10}$-aryl, more preferably phenyl, which aryl group, more preferably phenyl, is either unsubstituted or contains 1, 2, 3, 4 or 5 identical or different substituents; and NHC represents an N-heterocyclic carbene ligand.

The novel complexes of general formula (I) can be prepared according to various routes.

Hence the present invention also relates to processes for preparing the complexes of general formula (I).

The novel Ru and Os based complexes of general formula (I) are excellently suited for a broad variety of hydrogenation reactions.

Therefore, the present invention also relates to a process for manufacturing partially or fully saturated compounds by contacting unsaturated compounds containing at least one C=C double bond with hydrogen in the presence of at least one compound according to general formula (I).

BRIEF DESCRIPTION OF THE FIGURES

The aspects, features and advantages of this invention will become apparent from the following detailed description in conjunction with the accompanying figures showing the following:

FIG. 1 shows the percentage of residue double bonds ("RDB") depending on hydrogenation time for Comparative Examples 1 and 2 and Examples 3 to 8.

FIG. 2 shows the percentage of residue double bonds ("RDB") depending on hydrogenation time for Examples 4, and 9 to 11.

FIG. 3 shows the percentage of residue double bonds ("RDB") depending on hydrogenation time for Examples 4 and 12.

FIG. 4 shows the structure of complex (Ia)-SIMes as determined by single crystal XRD analysis.

DETAILED DESCRIPTION OF THE INVENTION

The novel catalysts according to general formula (I) are excellently suited for hydrogenating a broad variety of unsaturated compounds, whether these unsaturated compounds are low molecular weight substances, oligomers or polymers. The novel catalysts according to general formula (I) are in particular suited for hydrogenating unsaturated polymers like nitrile rubber showing a very high hydrogenation activity so that the use of co-catalysts is no longer necessary and the amount of catalyst to be used is so low that a later removal and recycling of the catalyst may be skipped. In one embodiment of the invention nitrile rubber can be hydrogenated to more than 90% conversion within 4 hours using the novel complex catalyst with an extreme low Ru metal loading of e.g. ~22 ppm of Ru (corresponding to 0.015 phr of the complex catalyst).

The novel complex catalysts show a very high stability when being exposed to air or water. Additionally and very surprisingly the novel complex catalysts may be used at substantially lower hydrogenation temperatures. With regard to the hydrogenation of nitrile rubber it was shown that the novel catalysts are already very active at 65° C. only. This is unexpected as other ruthenium based Schiff base catalysts known from prior art are only active at more elevated temperatures. If nitrile rubber is hydrogenated in the presence of the novel complexes the resulting hydrogenated nitrile rubber does not show any gel formation.

The term "substituted" used for the purposes of the present patent application means that a hydrogen atom on an indicated radical or atom has been replaced by another group or moiety, with the proviso that the valency of the atom indicated is not exceeded and the substitution leads to a stable compound.

For the purposes of the present patent application and invention, all the definitions of moieties, parameters or explanations given above or below in general terms or in preferred ranges can be combined with one another in any way and shall be considered as disclosed this way, i.e. including combinations of the respective ranges and preferred ranges.

Complex Catalyst:

In a preferred embodiment the present invention provides complexes of general formula (I) wherein
M is ruthenium
Y is H or Cl,
$R^1$, $R^2$, $R^3$, and $R^4$ are identical or different and represent
H; $NO_2$; F, Cl, or Br; or
straight chain or branched, substituted or unsubstituted $C_1$-$C_8$-alkyl, more preferably methyl, ethyl, n-propyl, i-propyl, n-butyl, i-butyl, or tert.-butyl; or
substituted or unsubstituted $C_5$-$C_8$-cycloalkyl, more preferably cyclopentyl, cyclohexyl or cycloheptyl; or
substituted or unsubstituted $C_6$-$C_{14}$-aryl, preferably $C_6$-$C_{10}$-aryl, more preferably phenyl, which aryl group, more preferably phenyl, is either unsubstituted or contains 1, 2, 3, 4 or 5 identical or different substituents; or
$OR^7$, $OC(=O)R^7$, $CO(=O)R^7$, $SO_3R^7$, $SO_3N(R^7)_2$ or $SO_3Na$ wherein $R^7$ represents H, straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl;
$R^5$ represents H; or
straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl; or
substituted or unsubstituted $C_3$-$C_{10}$-cycloalkyl, preferably $C_5$-$C_8$-cycloalkyl, more preferably cyclopentyl, cyclohexyl or cycloheptyl; or
substituted or unsubstituted $C_6$-$C_{14}$-aryl, preferably $C_6$-$C_{10}$-aryl, more preferably phenyl, which aryl group, more preferably phenyl, is either unsubstituted or contains 1, 2, 3, 4 or 5 identical or different substituents, even more preferably 1, 2 or 3 identical or different substituents which are located in the o- and/or p-positions and which are selected from the group consisting of $C_1$-$C_8$ alkyl, particularly methyl, ethyl, n-propyl, i-propyl, n-butyl, i-butyl, and tert.-butyl, halogen, particularly Cl, Br, and I, $OR^7$, $OC(=O)R^7$, and $CO(=O)R^7$ wherein $R^7$ represents H, straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, and tert.-butyl;
$R^6$ represents H, or
straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl;
substituted or unsubstituted $C_3$-$C_{10}$-cycloalkyl, preferably $C_5$-$C_8$-cycloalkyl, more preferably cyclopentyl, cyclohexyl or cycloheptyl; or
substituted or unsubstituted $C_6$-$C_{14}$-aryl, preferably $C_6$-$C_{10}$-aryl, more preferably phenyl, which aryl group, more preferably phenyl is either unsubstituted or contains 1, 2, 3, 4 or 5 identical or different substituents; and
NHC represents an N-heterocyclic carbene ligand, preferably an N-heterocyclic carbene ligand selected from formulae (IIa) to (IIe) as defined below, more preferably an N-heterocyclic carbene ligand selected from formulae (IIIa) to (IIIu) as defined below.

In an even more preferred embodiment the present invention provides complexes of general formula (I) wherein
M is ruthenium
Y is H or Cl,
$R^1$, $R^2$, $R^3$, and $R^4$ are all H or $R^1$, $R^3$, and $R^4$ are all H while $R^2$ is simultaneously $NO_2$;
$R^5$ represents H;
straight chain or branched, substituted or unsubstituted $C_1$-$C_8$-alkyl, more preferably methyl, ethyl, n-propyl, i-propyl, n-butyl, i-butyl, or tert.-butyl; or
substituted or unsubstituted $C_5$-$C_8$-cycloalkyl, more preferably cyclopentyl, cyclohexyl or cycloheptyl; or
substituted or unsubstituted $C_6$-$C_{10}$-aryl, more preferably phenyl, which aryl group, more preferably phenyl, is either unsubstituted or contains 1, 2, 3, 4 or 5 identical or different substituents, even more preferably 1, 2 or 3 identical or different substituents which are located in the o- and/or p-positions and which are selected from the group consisting of $C_1$-$C_8$ alkyl, particularly methyl, ethyl, n-propyl, i-propyl, n-butyl, i-butyl, and tert.-butyl, halogen, particularly Cl, Br, and I, $OR^7$, $OC(=O)R^7$, and $CO(=O)R^7$ wherein $R^7$ represents H, straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, and tert.-butyl;

$R^6$ represents H, or straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl; or substituted or unsubstituted $C_3$-$C_{10}$-cycloalkyl, preferably $C_5$-$C_8$-cycloalkyl, more preferably cyclopentyl, cyclohexyl or cycloheptyl; or substituted or unsubstituted $C_6$-$C_{14}$-aryl, preferably $C_6$-$C_{10}$-aryl, more preferably phenyl, which aryl group, more preferably phenyl, is either unsubstituted or contains 1, 2, 3, 4 or 5 identical or different substituents; and NHC represents an N-heterocyclic carbene ligand, preferably an N-heterocyclic carbene ligand selected from formulae (IIa) to (IIe) as defined below, more preferably an N-heterocyclic carbene ligand selected from formulae (IIIa) to (IIIu) as defined below.

NHC-Ligand:

In the general formula (I) the N-heterocyclic carbene ligand represents a cyclic carbene type ligand with at least one nitrogen as hetero atom being present in the ring. The ring can exhibit different substitution patterns on the ring atoms. Preferably this substitution pattern provides a certain degree of steric crowing.

In the context of this invention the N-heterocyclic carbene ligand(s) (hereinafter referred to as "NHC-ligand(s) and depicted as "NHC" in the general formulae) is/are preferably based on imidazoline or imidazolidine moieties.

In the general formula (I) as disclosed above with the general as well as the preferred, more preferred and particularly preferred meanings of M, Y, $R^1$-$R^6$ the NHC-ligand typically has a structure corresponding to the general formulae (IIa) to (IIe)

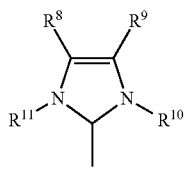
(IIa)

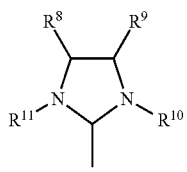
(IIb)

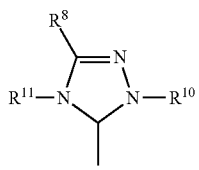
(IIc)

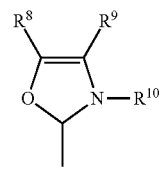
(IId)

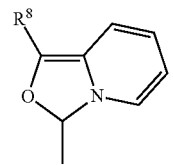
(IIe)

wherein $R^8$, $R^9$, $R^{10}$ and $R^{11}$ are identical or different and represent hydrogen, straight-chain or branched $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, $C_7$-$C_{25}$-alkaryl, $C_2$-$C_{20}$-heteroaryl, $C_2$-$C_{20}$-heterocyclyl, $C_1$-$C_{20}$-alkoxy, $C_2$-$C_{20}$-alkenyloxy, $C_2$-$C_{20}$-alkynyloxy, $C_6$-$C_{20}$-aryloxy, $C_2$-$C_{20}$-alkoxycarbonyl, $C_1$-$C_{20}$-alkylthio, $C_6$-$C_{20}$-arylthio, $-Si(R)_3$, $-O-Si(R)_3$, $-O-C(=O)R$, $C(=O)R$, $-C(=O)N(R)_2$, $-NR-C(=O)-N(R)_2$, $-SO_2N(R)_2$, $-S(=O)R$, $-S(=O)_2R$, $-O-S(=O)_2R$, halogen, nitro or cyano; wherein in all above occurrences relating to the meanings of $R^8$, $R^9$, $R^{10}$ and $R^{11}$ the group R is identical or different and represents hydrogen, $C_1$-$C_{30}$-alkyl, $C_3$-$C_{20}$-cycloalkyl, $C_2$-$C_{20}$-alkenyl, $C_2$-$C_{20}$-alkynyl, $C_6$-$C_{24}$-aryl, or $C_2$-$C_{20}$-heteroaryl.

In these formulae (IIa) to (IIe) the carbon atom bonding to the Ruthenium or Osmium metal center is formally a carbene carbon.

If appropriate, one or more of $R^8$, $R^9$, $R^{10}$, and $R^{11}$ can independently of one another, be substituted by one or more substituents, preferably straight-chain or branched $C_1$-$C_{10}$-alkyl, $C_3$-$C_8$-cycloalkyl, $C_1$-$C_{10}$-alkoxy, $C_6$-$C_{24}$-aryl, $C_2$-$C_{20}$-heteroaryl, $C_2$-$C_{20}$-heterocyclyl, and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen, wherein the abovementioned substituents, to the extent chemically possible, may in turn be substituted by one or more substituents, preferably selected from the group consisting of halogen, in particular chlorine or bromine, $C_1$-$C_5$-alkyl, $C_1$-$C_5$-alkoxy and phenyl.

Merely for the sake of clarity, it may be added that the structures of the NHC-ligand depicted in the general formulae (IIa) and (IIb) in the present patent application are equivalent to the structures (IIa-(i)) and (IIb-(i)) which are frequently also found in the literature for such NHC-ligands, respectively, and emphasize the carbene character of the NHC-ligand. This applies analogously to the further structures (IIc) to (IIe) as well as the associated preferred structures (IIIa)-(IIIu) depicted below.

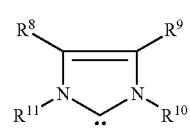
(IIa-(i))

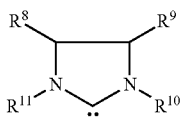

(IIb-(i))

In preferred NHC-ligand(s) in the catalysts of the general formula (I)
R$^8$ and R$^9$ are identical or different and represent hydrogen, C$_6$-C$_{24}$-aryl, more preferably phenyl, straight-chain or branched C$_1$-C$_{10}$-alkyl, more preferably methyl, ethyl, n-propyl, i-propyl, n-butyl, sec-butyl, i-butyl or tert.-butyl or form a cycloalkyl or aryl structure together with the carbon atoms to which they are bound.

The preferred and more preferred meanings of R$^8$ and R$^9$ may be either unsubstituted or substituted by one or more further substituents selected from the group consisting of straight-chain or branched C$_1$-C$_{10}$-alkyl or C$_1$-C$_{10}$-alkoxy, C$_3$-C$_8$-cycloalkyl, C$_6$-C$_{24}$-aryl, and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen, wherein all these substituents may in turn be either unsubstituted or substituted by one or more substituents, preferably selected from the group consisting of halogen, in particular chlorine or bromine, C$_1$-C$_5$-alkyl, C$_1$-C$_5$-alkoxy and phenyl.

In further preferred NHC-ligand(s) in the catalysts of the general formula (I)
R$^{10}$ and R$^{11}$ are identical or different and preferably represent straight-chain or branched C$_1$-C$_{10}$-alkyl, more preferably i-propyl or neopentyl, C$_3$-C$_{10}$-cycloalkyl, more preferably adamantyl, substituted or unsubstituted C$_6$-C$_{24}$-aryl, more preferably phenyl, 2,6-diisopropylphenyl, 2,6-dimethylphenyl, or 2,4,6-trimethylphenyl, C$_1$-C$_{10}$-alkylsulfonate, or C$_6$-C$_{10}$-arylsulfonate.

These preferred meanings of R$^{10}$ and R$^{11}$ may be either unsubstituted or substituted by one or more further substituents selected from the group consisting of straight-chain or branched C$_1$-C$_{10}$-alkyl or C$_1$-C$_{10}$-alkoxy, C$_3$-C$_8$-cycloalkyl, C$_6$-C$_{24}$-aryl, and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen, wherein all these substituents may in turn be either unsubstituted or substituted by one or more substituents, preferably selected from the group consisting of halogen, in particular chlorine or bromine, C$_1$-C$_5$-alkyl, C$_1$-C$_5$-alkoxy and phenyl.

In further preferred NHC-ligand(s) in the catalysts of the general formula (I)
R$^8$ and R$^9$ are identical or different and represent hydrogen, C$_6$-C$_{24}$-aryl, more preferably phenyl, straight-chain or branched C$_1$-C$_{10}$-alkyl, more preferably methyl, ethyl, n-propyl, i-propyl, n-butyl, sec-butyl, and i-butyl, or form a cycloalkyl or aryl structure together with the carbon atoms to which they are bound, and
R$^{10}$ and R$^{11}$ are identical or different and preferably represent straight-chain or branched C$_1$-C$_{10}$-alkyl, more preferably i-propyl or neopentyl, C$_3$-C$_{10}$-cycloalkyl, more preferably adamantyl, substituted or unsubstituted C$_6$-C$_{24}$-aryl, more preferably phenyl, 2,6-diisopropylphenyl, 2,6-dimethylphenyl, 2,4,6-trimethylphenyl, C$_1$-C$_{10}$-alkylsulfonate, or C$_6$-C$_{10}$-arylsulfonate, wherein all such meanings of R$^8$, R$^9$, R$^{10}$ and R$^{11}$ can be unsubstituted or substituted with the same substitution pattern as outlined above with respect to the R$^8$ and R$^9$, on the one hand, and R$^{10}$ and R$^{11}$, on the other hand.

Particularly preferred NHC-ligands have the following structures (IIIa) to (IIIu), where "Ph" means in each case phenyl, "Bu" means in each case butyl, i.e. either n-butyl, sec.-butyl, iso-butyl or tert.-butyl, "Mes" represents in each case 2,4,6-trimethylphenyl, "Dipp" means in all cases 2,6-diisopropylphenyl and "Dimp" means in each case 2,6-dimethylphenyl.

(IIIa)

(IIIb)

(IIIc)

(IIId)

(IIIe)

(IIIf)

(IIIg)

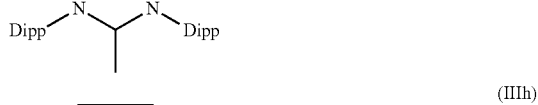
(IIIh)

(IIIj)

-continued

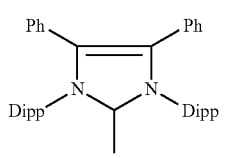
(IIIk)

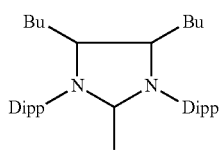
(IIIm)

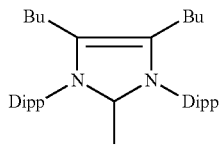
(IIIn)

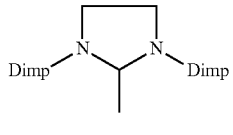
(IIIp)

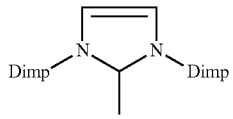
(IIIq)

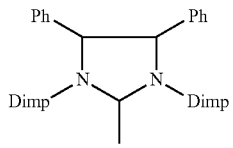
(IIIr)

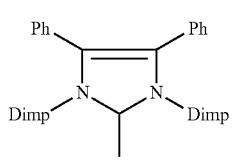
(IIIs)

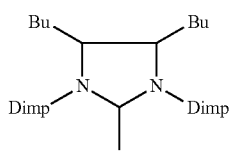
(IIIt)

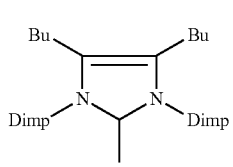
(IIIu)

Where the NHC-ligand contains not only an "N" (nitrogen), but also an "O" (oxygen) in the ring it is preferred that the substitution pattern of $R^8$, $R^9$, $R^{10}$ and/or $R^{11}$ provides a certain steric crowding.

Process for Preparing the Ruthenium or Osmium Based Complexes of General Formula (I)

The novel highly active catalysts can be synthesized starting from cheaply available raw materials and three different routes are available as possible pathways:

Route 1:

According to Route 1 the compounds of general formula (I) can be manufactured by reacting a compound of general formula (1)

$$MXY(CO)(PR_3)_n \qquad (1)$$

wherein

M is ruthenium or osmium, preferably ruthenium;

X is H, Cl, Br or I;

Y represents H, F, Cl, Br, I, $CF_3$, pyridine, —$OC_6H_5$, $CF_3COO$—, $CH_3SO_3$—, or $BF_4$;

R represents
 substituted or unsubstituted $C_1$-$C_{14}$-alkyl, preferably $C_1$-$C_6$-alkyl;
 substituted or unsubstituted $C_3$-$C_8$-cycloalkyl, preferably cyclopentyl, cyclohexyl or cycloheptyl;
 substituted or unsubstituted $C_6$-$C_{14}$-aryl, preferably substituted or unsubstituted phenyl, more preferably phenyl; and n is 3, if R represent substituted or unsubstituted $C_6$-$C_{14}$-aryl, preferably substituted or unsubstituted phenyl, more preferably phenyl; or n is 2, if R represent substituted or unsubstituted $C_1$-$C_{14}$-alkyl, preferably $C_1$-$C_6$-alkyl or substituted or unsubstituted $C_3$-$C_8$-cycloalkyl, preferably cyclopentyl, cyclohexyl or cycloheptyl;

with a compound of general formula (2)

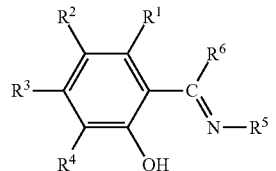
(2)

wherein $R^1$, $R^2$, $R^3$, and $R^4$ are identical or different and represent H; $NO_2$; $CF_3$; halogen, preferably F, Cl, Br, or I; or
 straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl;
 substituted or unsubstituted $C_3$-$C_{10}$-cycloalkyl, preferably $C_5$-$C_8$-cycloalkyl, more preferably cyclopentyl, cyclohexyl or cycloheptyl;
 substituted or unsubstituted $C_6$-$C_{14}$-aryl, preferably $C_6$-$C_{10}$-aryl, more preferably phenyl, which aryl group, more preferably phenyl, is either unsubstituted or contains 1, 2, 3, 4 or 5 identical or different substituents;
 $OR^7$, $OC(=O)R^7$, $CO(=O)R^7$, $SO_3R^7$, $SO_3N(R^7)_2$ or $SO_3Na$ wherein $R^7$ represents H, straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl;
 $(N(R^8)_3)^+X^-$ wherein X is halide, preferably chloride, and $R^8$ are identical or different and represent H; straight chain or branched, substituted or unsubstituted $C_1$-$C_{14}$ alkyl, preferably $C_1$-$C_8$-alkyl, more preferably methyl, ethyl, n-propyl, i-propyl, n-butyl, i-butyl, or tert.-butyl; substituted or unsubstituted $C_6$-$C_{14}$-aryl, preferably $C_6$-$C_{10}$-aryl, more preferably phenyl, which aryl group, more preferably phenyl, is either unsubstituted or contains 1, 2, 3, 4 or 5 identical or different substituents; most preferably $N(CH_3)(C_2H_5)_2{}^+Cl^-$, $N(C_2H_5)_2H^+Cl^-$, $NH_3{}^+Cl^-$, $NH(CH_3)_2Cl^-$, or $N(CH_3)_3{}^+Cl^-$;

tris $(C_1$-$C_6$-alkoxy)silyl-$C_1$-$C_6$-alkyl, tris $(C_6$-$C_{14}$-aryloxy)silyl-$C_1$-$C_6$-alkyl, or tris$(C_3$-$C_{10}$-cycloalkoxy)silyl-$C_1$-$C_6$-alkyl, preferably trisethoxysilyl-n-propyl;

$R^5$ represents H;

straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, and tert.-butyl;

substituted or unsubstituted $C_3$-$C_{10}$-cycloalkyl, preferably $C_5$-$C_8$-cycloalkyl, more preferably cyclopentyl, cyclohexyl or cycloheptyl;

substituted or unsubstituted $C_6$-$C_{14}$-aryl, preferably $C_6$-$C_{10}$-aryl, more preferably phenyl, which aryl group, more preferably phenyl, is either unsubstituted or contains 1, 2, 3, 4 or 5 identical or different substituents, even more preferably 1, 2 or 3 identical or different substituents which are located in the o- and/or p-positions;

$R^6$ represents H, or straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl; or substituted or unsubstituted $C_3$-$C_{10}$-cycloalkyl, preferably $C_5$-$C_8$-cycloalkyl, more preferably cyclopentyl, cyclohexyl or cycloheptyl; or substituted or unsubstituted $C_6$-$C_{14}$-aryl, preferably $C_6$-$C_{10}$-aryl, more preferably phenyl, which aryl group, more preferably phenyl, is either unsubstituted or contains 1, 2, 3, 4 or 5 identical or different substituents; and to yield a compound of general formula (3)

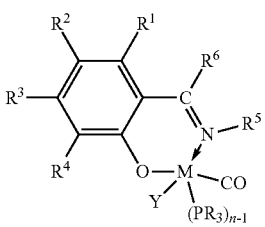

(3)

wherein $R^1$, $R^2$, $R^3$, $R^4$, $R^5$, $R^6$, n, M, Y and R shall have the same general, preferred and more preferred meanings as outlined above for general formulae (1) and (2).

which is then reacted with an N-heterocyclic carbene to yield the compounds of general formula (I).

Further Typical Reaction Parameters:

The process according to Route 1 is typically performed in one or more organic solvents, preferably selected from the group consisting of ethers, more preferably THF, dioxane, and diethylether, alkanes, more preferably hexane, aromatic solvents, more preferably toluene, and benzene, halogenated hydrocarbon, more preferably chloroform and chlorobenzene, ester, more preferably ethyl acetate, ketone, more preferably methyl ethyl ketone, acetone, and alcohols, more preferably methanol, ethanol and methyloxyethanol. Further on the process pursuant to route 1 is typically performed either without any catalyst or in the presence of at least one catalyst, preferably $Ag_2CO_3$ or TlOEt.

The Process Pursuant to Route 1 is Shown in Total in the Following Scheme:

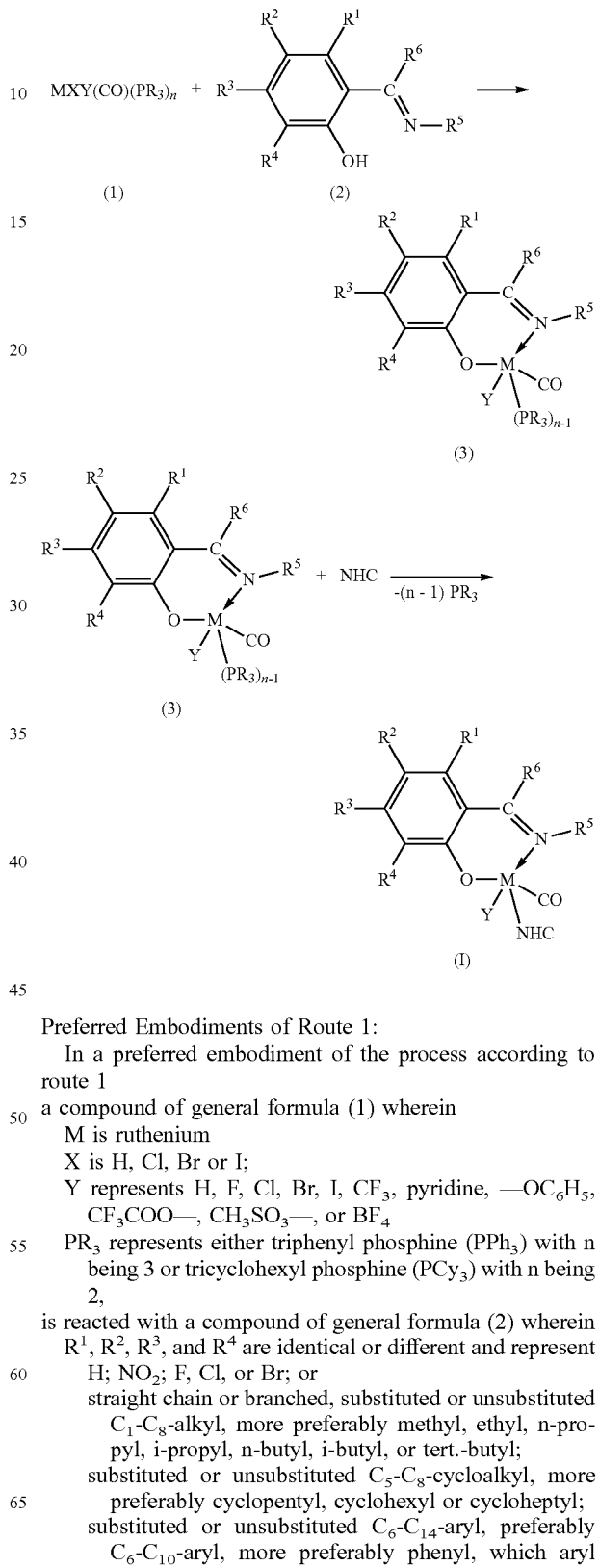

Preferred Embodiments of Route 1:

In a preferred embodiment of the process according to route 1 a compound of general formula (1) wherein

M is ruthenium

X is H, Cl, Br or I;

Y represents H, F, Cl, Br, I, $CF_3$, pyridine, —$OC_6H_5$, $CF_3COO$—, $CH_3SO_3$—, or $BF_4$ $PR_3$ represents either triphenyl phosphine ($PPh_3$) with n being 3 or tricyclohexyl phosphine ($PCy_3$) with n being 2, is reacted with a compound of general formula (2) wherein $R^1$, $R^2$, $R^3$, and $R^4$ are identical or different and represent H; $NO_2$; F, Cl, or Br; or straight chain or branched, substituted or unsubstituted $C_1$-$C_8$-alkyl, more preferably methyl, ethyl, n-propyl, i-propyl, n-butyl, i-butyl, or tert.-butyl;

substituted or unsubstituted $C_5$-$C_8$-cycloalkyl, more preferably cyclopentyl, cyclohexyl or cycloheptyl;

substituted or unsubstituted $C_6$-$C_{14}$-aryl, preferably $C_6$-$C_{10}$-aryl, more preferably phenyl, which aryl group, more preferably phenyl, is either unsubstituted or contains 1, 2, 3, 4 or 5 identical or different substituents;

OR$^7$, OC(=O)R$^7$, CO(=O)R$^7$, SO$_3$R$^7$, SO$_3$N(R$^7$)$_2$ or SO$_3$Na wherein R$^7$ represents H, straight chain or branched, substituted or unsubstituted C$_1$-C$_{14}$-alkyl, preferably C$_1$-C$_8$-alkyl, more preferably methyl, ethyl, n-propyl, i-propyl, n-butyl, i-butyl, or tert.-butyl;

R$^5$ straight chain or branched C$_1$-C$_8$-alkyl, more preferably methyl, ethyl, n-propyl, i-propyl, n-butyl, i-butyl, or tert.-butyl which is either unsubstituted or substituted with OR$^7$, OC(=O)R$^7$, or CO(=O)R$^7$, wherein R$^7$ represents H, straight chain or branched, substituted or unsubstituted C$_1$-C$_{14}$-alkyl, preferably C$_1$-C$_8$-alkyl, more preferably methyl, ethyl, n-propyl, i-propyl, n-butyl, i-butyl, or tert.-butyl;

substituted or unsubstituted C$_6$-C$_{14}$-aryl, preferably C$_6$-C$_{10}$-aryl, more preferably phenyl, which is either unsubstituted or which contains 1, 2, 3, 4 or 5 identical or different substituents, even more preferably 1, 2 or 3 identical or different substituents which are located in the o- and/or p-positions and which are selected from the group consisting of C$_1$-C$_8$ alkyl, particularly methyl, ethyl, n-propyl, i-propyl, n-butyl, i-butyl, and tert.-butyl, halogen, particularly Cl, Br, and I, OR$^7$, OC(=O)R$^7$, and CO(=O)R$^7$ wherein R$^7$ represents H, straight chain or branched, substituted or unsubstituted C$_1$-C$_{14}$-alkyl, preferably C$_1$-C$_8$-alkyl, more preferably methyl, ethyl, n-propyl, i-propyl, n-butyl, i-butyl, or tert.-butyl;

R$^6$ represents H, or straight chain or branched, substituted or unsubstituted C$_1$-C$_{14}$-alkyl, preferably C$_1$-C$_8$-alkyl, more preferably methyl, ethyl, n-propyl, i-propyl, n-butyl, i-butyl, or tert.-butyl; or substituted or unsubstituted C$_3$-C$_{10}$-cycloalkyl, preferably C$_5$-C$_8$-cycloalkyl, more preferably cyclopentyl, cyclohexyl or cycloheptyl; or substituted or unsubstituted C$_6$-C$_{14}$-aryl, preferably C$_6$-C$_{10}$-aryl, more preferably phenyl, which aryl group, more preferably phenyl, is either unsubstituted or contains 1, 2, 3, 4 or 5 identical or different substituents; and to yield a compound of general formula (3) wherein M is ruthenium R$^1$, R$^2$, R$^3$, R$^4$, R$^5$, R$^6$, n, Y and R shall have the same meanings as outlined above for the above preferred embodiments of general formulae (1) and (2), which is then reacted with a N-heterocyclic carbene to result in the compound of general formula (I) wherein R$^1$, R$^2$, R$^3$, R$^4$, R$^5$, R$^6$, NHC, and Y shall have the same meanings as outlined above for the preferred embodiments of general formulae (1) and (2).

Typical and Preferred Compounds (1):

Compound (1) is typically either commercially available or can be synthesized according to processes known to a person skilled in the art.

Preferably the following compounds of general formula (1) can be used: RuHCl(CO)(PR$_3$)$_n$, RuH$_2$(CO)(PR$_3$)$_n$, or RuCl$_2$(CO)(PR$_3$)$_n$ wherein R and n shall have the meanings defined above for general formula (I).

More preferably the following compounds of general formula (1) can be used: RuHCl(CO)(PCy$_3$)$_2$, RuHCl(CO)(PPh$_3$)$_3$, RuCl$_2$(CO)(PCy$_3$)$_2$, RuCl$_2$(CO)(PPh$_3$)$_3$, RuH$_2$(CO)(PCy$_3$)$_2$, or RuH$_2$(CO)(PPh$_3$)$_3$.

RuHCl(CO)(PCy$_3$)$_2$ and RuHCl(CO)(PPh$_3$)$_3$ can be prepared from RuCl$_3$ and the corresponding phosphine in alcohol easily according to Journal of Molecular Catalysis A: Chemical, 1997, 126, 115 for RuHCl(CO)(PCy$_3$)$_2$ and Inorg. Synth. 1974, 15, 48 for RuHCl(CO)(PPh$_3$)$_3$.

RuCl$_2$(CO)(PCy$_3$)$_2$ can be prepared from RuCl$_3$ and PCy$_3$ in the presence of CO pursuant to Journal of Organometallic Chemistry, 1974, 65, 93.

RuCl$_2$(CO)(PPh$_3$)$_3$ can be prepared following Comprehensive Organometallic Chemistry 1982, Vol 4, chapter 32.9.

RuH$_2$(CO)(PPh$_3$)$_3$ is commercially available, e.g. from Strem.

Typical and Preferred Compounds (2):

Compounds of general formula (2) represent Schiff bases and can be easily prepared from salicylaldehyde and the respective primary amine. Such preparation is well known in the art.

Preferred examples of the compounds of general formula (2) are the following.

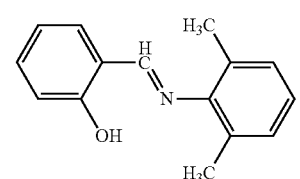

(2a)

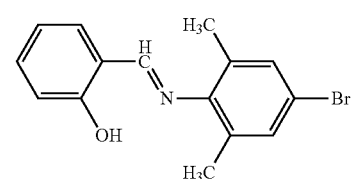

(2b)

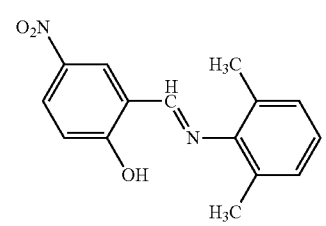

(2c)

Preferred Compounds (3):

Upon converting the preferred starting materials of formulae (2a), (2b) and (2c) with compounds of general formula (1) the following compounds (3) are for example obtained:

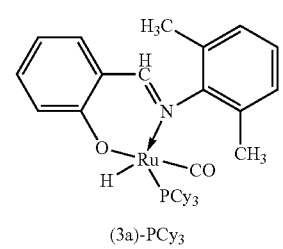

(3a)-PCy$_3$

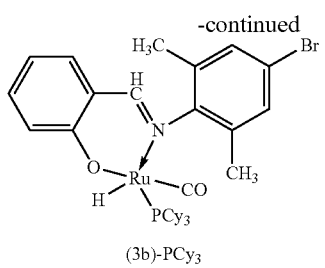

(3b)-PCy₃

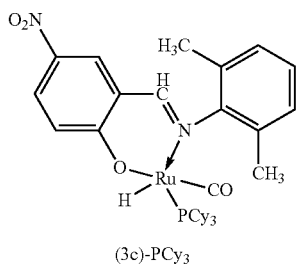

(3c)-PCy₃

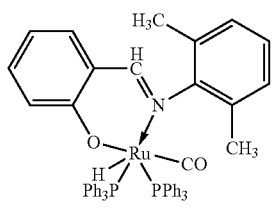

(3a)-PPh₃

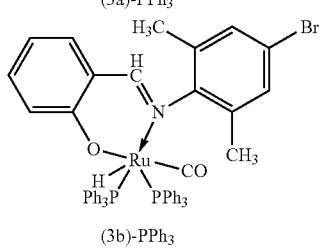

(3b)-PPh₃

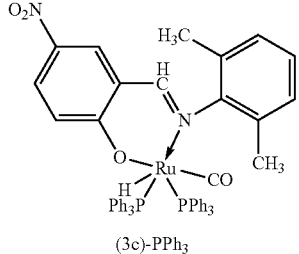

(3c)-PPh₃

Preferred Complexes of General Formula (I)

By further conversion of the preferred compounds of the above formulae (3) with an N-heterocyclic carbene the following preferred complexes falling under formula (I) can be obtained when the following N-heterocyclic carbenes are used:

"IMes" which means N,N'-bis(mesityl)imidazol-2-ylidene, or

"SIMes" which means N,N'-bis(mesityl)imidazolidin-2-ylidene, or

"IPr" which means N,N'-bis(2,6-diisopropylphenyl)imidazol-2-ylidene or

"ItBu" which means N,N'-bis(tert-butyl)imidazol-2-ylidene

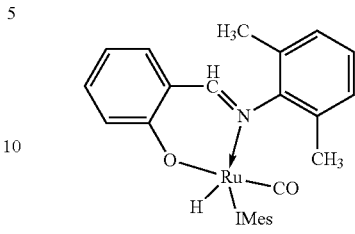

(Ia)-IMes

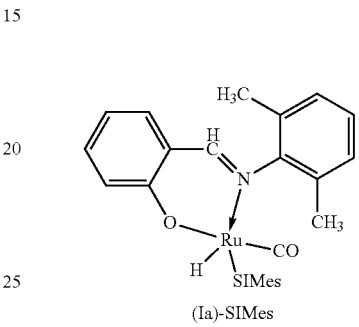

(Ia)-SIMes

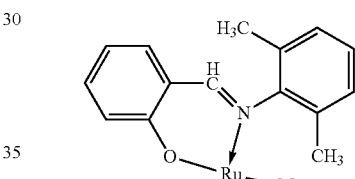

(Ia)-IPr

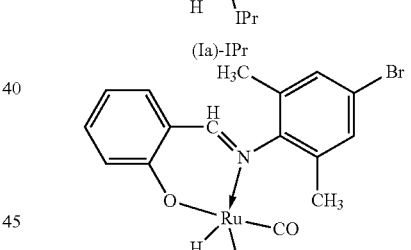

(Ib)-IMes

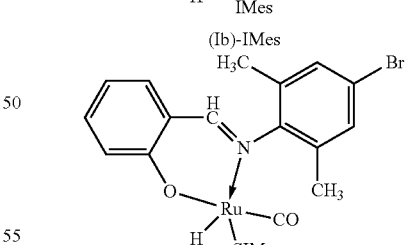

(Ib)-SIMes

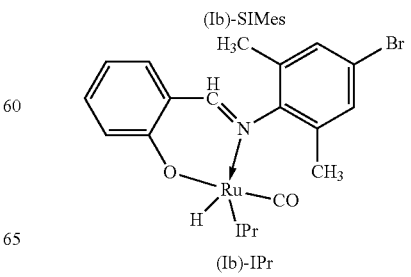

(Ib)-IPr

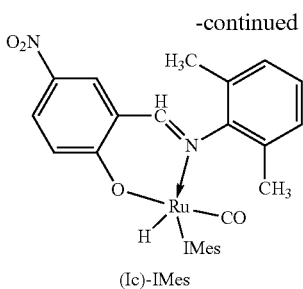

(Ic)-IMes

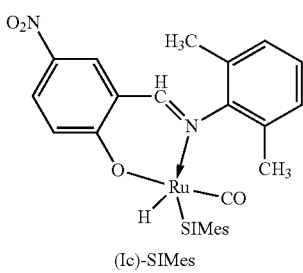

(Ic)-SIMes

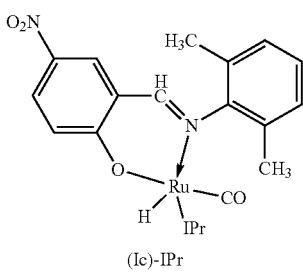

(Ic)-IPr

Route 2:

According to Route 2 the compounds of general formula (I) can be manufactured by reacting a compound of general formula (4)

MXY(CO)(NHC)(PR$_3$)          (4)

wherein

M is ruthenium or osmium, preferably ruthenium,

X is H, Cl, Br or I;

Y represents H, F, Cl, Br, I, CF$_3$, pyridine, —OC$_6$H$_5$, CF$_3$COO—, CH$_3$SO$_3$—, or BF$_4$ R is identical or different, preferably identical and represents substituted or unsubstituted C$_1$-C$_{14}$-alkyl, preferably C$_1$-C$_6$-alkyl;

substituted or unsubstituted C$_3$-C$_8$-cycloalkyl, preferably cyclopentyl, cyclohexyl or cycloheptyl;

substituted or unsubstituted C$_6$-C$_{14}$-aryl, preferably substituted or unsubstituted phenyl, more preferably phenyl; and n is 3, if R represent substituted or unsubstituted C$_6$-C$_{14}$-aryl, preferably substituted or unsubstituted phenyl, more preferably phenyl; or n is 2, if R represent substituted or unsubstituted C$_1$-C$_{14}$-alkyl, preferably C$_1$-C$_6$-alkyl or substituted or unsubstituted C$_3$-C$_8$-cycloalkyl, preferably cyclopentyl, cyclohexyl or cycloheptyl; and NHC is an N-heterocyclic carbene;

with a compound of general formula (2)

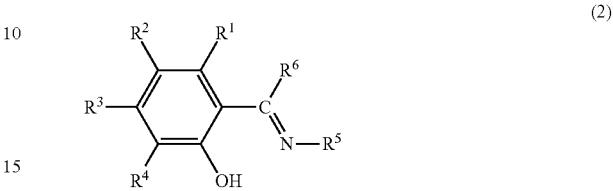

(2)

wherein

R$^1$, R$^2$, R$^3$, and R$^4$ are identical or different and represent

H; NO$_2$; CF$_3$; halogen, preferably F, Cl, Br, or I; or straight chain or branched, substituted or unsubstituted C$_1$-C$_{14}$-alkyl, preferably C$_1$-C$_8$-alkyl, more preferably methyl, ethyl, n-propyl, i-propyl, n-butyl, i-butyl, or tert.-butyl;

substituted or unsubstituted C$_3$-C$_{10}$-cycloalkyl, preferably C$_5$-C$_8$-cycloalkyl, more preferably cyclopentyl, cyclohexyl or cycloheptyl;

substituted or unsubstituted C$_6$-C$_{14}$-aryl, preferably C$_6$-C$_{10}$-aryl, more preferably phenyl, which aryl group, more preferably phenyl, is either unsubstituted or contains 1, 2, 3, 4 or 5 identical or different substituents;

OR$^7$, OC(=O)R$^7$, CO(=O)R$^7$, SO$_3$R$^7$, SO$_3$N(R$^7$)$_2$ or SO$_3$Na wherein R$^7$ represents H, straight chain or branched, substituted or unsubstituted C$_1$-C$_{14}$-alkyl, preferably C$_1$-C$_8$-alkyl, more preferably methyl, ethyl, n-propyl, i-propyl, n-butyl, i-butyl, or tert.-butyl;

(N(R$^8$)$_3$)$^+$X$^-$ wherein X is halide, preferably chloride, and R$^8$ are identical or different and represent H; straight chain or branched, substituted or unsubstituted C$_1$-C$_{14}$-alkyl, preferably C$_1$-C$_8$-alkyl, more preferably methyl, ethyl, n-propyl, i-propyl, n-butyl, i-butyl, and tert.-butyl; substituted or unsubstituted C$_6$-C$_{14}$-aryl, preferably C$_6$-C$_{10}$-aryl, more preferably phenyl, which aryl group is either unsubstituted or contains 1, 2, 3, 4 or 5 identical or different substituents; most preferably N(CH$_3$)(C$_2$H$_5$)$_2$$^+$Cl$^-$, N(C$_2$H$_5$)$_2$H$^+$Cl$^-$, NH$_3$$^+$Cl$^-$, NH(CH$_3$)$_2$$^+$Cl$^-$, or N(CH$_3$)$_3$$^+$Cl$^-$;

tris (C$_1$-C$_6$-alkoxy)silyl-C$_1$-C$_6$-alkyl, tris (C$_6$-C$_{14}$-aryloxy)silyl-C$_1$-C$_6$-alkyl, or tris(C$_3$-C$_{10}$-cycloalkoxy) silyl-C$_1$-C$_6$-alkyl, preferably trisethoxysilyl-n-propyl;

R$^5$ represents H;

straight chain or branched, substituted or unsubstituted C$_1$-C$_{14}$-alkyl, preferably C$_1$-C$_8$-alkyl, more preferably methyl, ethyl, n-propyl, i-propyl, n-butyl, i-butyl, or tert.-butyl;

substituted or unsubstituted C$_3$-C$_{10}$-cycloalkyl, preferably C$_5$-C$_8$-cycloalkyl, more preferably cyclopentyl, cyclohexyl or cycloheptyl;

substituted or unsubstituted C$_6$-C$_{14}$-aryl, preferably C$_6$-C$_{10}$-aryl, more preferably phenyl, which aryl group, more preferably phenyl, is either unsubstituted or contains 1, 2, 3, 4 or 5 identical or different substituents, even more preferably 1, 2 or 3 identical or different substituents which are located in the o- and/or p-positions;

$R^6$ represents H, or straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl; or substituted or unsubstituted $C_3$-$C_{10}$-cycloalkyl, preferably $C_5$-$C_8$-cycloalkyl, more preferably cyclopentyl, cyclohexyl or cycloheptyl; or substituted or unsubstituted $C_6$-$C_{14}$-aryl, preferably $C_6$-$C_{10}$-aryl, more preferably phenyl, which aryl group, more preferably phenyl, is either unsubstituted or contains 1, 2, 3, 4 or 5 identical or different substituents; and to yield a compound of general formula (I) wherein $R^1$, $R^2$, $R^3$, $R^4$, $R^5$, Y, M and R shall have the same general, preferred and more preferred meanings as outlined above for general formulae (2) and (4).

The Process Pursuant to Route 2 is Shown in Total in the Following Scheme:

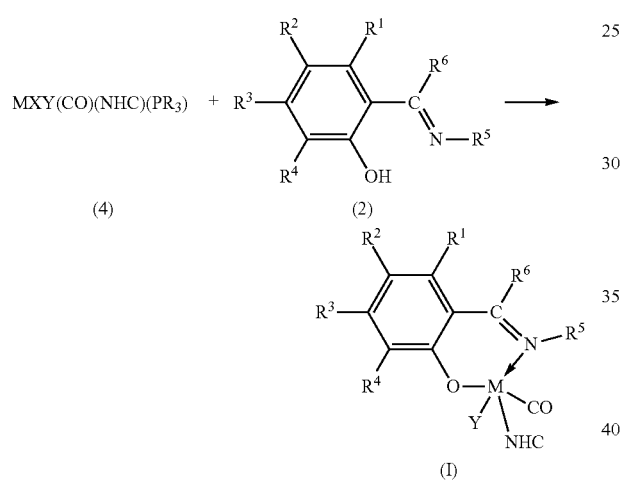

Typical and Preferred Compounds (4):

Typical examples of complex (4) include RuHCl(CO)(IMes)(PPh$_3$), RuHCl(CO)(SIMes)(PPh$_3$), RuHCl(CO)(IPr)(PPh$_3$), RuHCl(CO)(IMes)(PCy$_3$), RuHCl(CO)(SIMes)(PCy$_3$), and RuHCl(CO)(IPr)(PCy$_3$).

The synthesis of complex (4) can be performed according to processes disclosed in literature (see e.g. Organometallics, 2001, 20, 794 when R=Cy (meaning cyclohexyl) and Organometallics, 2005, 24, 1056 when R=Ph (meaning phenyl)).

Typical and Preferred Compounds (2):

The compounds of general formula (2) are the same as defined above for Route 1.

Further Typical Reaction Parameters:

The process according to route 2 is typically performed in one or more organic solvents, preferably selected from the group consisting of ethers, more preferably THF, dioxane, and diethylether, alkanes, more preferably hexane, aromatic solvents, more preferably toluene, and benzene, halogenated hydrocarbon, more preferably chloroform and chlorobenzene, ester, more preferably ethyl acetate, ketone, more preferably methyl ethyl ketone, acetone, and alcohols, more preferably methanol, ethanol and methyloxyethanol. Further on the process pursuant to route 2 is typically performed either without any catalyst or in the presence of at least one catalyst, preferably Ag$_2$CO$_3$ or TlOEt.

Route 3:

According to Route 3 the compounds of general formula (I) can be manufactured by reacting a compound of general formula (5)

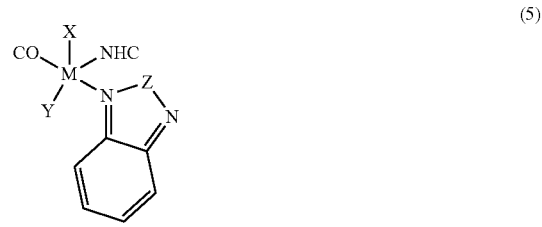

wherein

X is H, Cl, Br or I;

Y represents H, F, Cl, Br, I, CF$_3$, pyridine, —OC$_6$H$_5$, CF$_3$COO—, CH$_3$SO$_3$—, or BF$_4$ and NHC is an N-heterocyclic carbene; and Z is either S or Se with a compound of general formula (2)

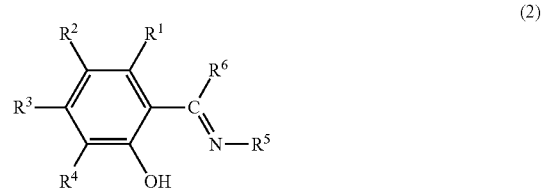

wherein $R^1$, $R^2$, $R^3$, and $R^4$ are identical or different and represent H; NO$_2$; CF$_3$; halogen, preferably F, Cl, Br, or I; or straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl;

substituted or unsubstituted $C_3$-$C_{10}$-cycloalkyl, preferably $C_5$-$C_8$-cycloalkyl, more preferably cyclopentyl, cyclohexyl or cycloheptyl;

substituted or unsubstituted $C_6$-$C_{14}$-aryl, preferably $C_6$-$C_{10}$-aryl, more preferably phenyl, which aryl group, more preferably phenyl, is either unsubstituted or contains 1, 2, 3, 4 or 5 identical or different substituents;

OR$^7$, OC(=O)R$^7$, CO(=O)R$^7$, SO$_3$R$^7$, SO$_3$N(R$^7$)$_2$ or SO$_3$Na wherein R$^7$ represents H, straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, or tert.-butyl;

(N(R$^8$)$_3$)$^+$X$^-$ wherein X is halide, preferably chloride, and R$^8$ are identical or different and represent H; straight chain or branched, substituted or unsubstituted $C_1$-$C_{14}$-alkyl, preferably $C_1$-$C_8$-alkyl, more preferably methyl, ethyl, n-propyl, i-propyl, n-butyl, i-butyl, and tert.-butyl; substituted or unsubstituted $C_6$-$C_{14}$-aryl, preferably $C_6$-$C_{10}$-aryl, more preferably phenyl, which aryl group is either unsubstituted or contains 1, 2, 3, 4 or 5 identical or different substituents; most preferably N(CH$_3$)(C$_2$H$_5$)$_2$$^+$Cl$^-$, N(C$_2$H$_5$)$_2$H$^+$Cl$^-$, NH$_3$$^+$Cl$^-$, NH(CH$_3$)$_2$$^+$Cl$^-$, or N(CH$_3$)$_3$$^+$Cl$^-$;

tris (C$_1$-C$_6$-alkoxy)silyl-C$_1$-C$_6$-alkyl, tris (C$_6$-C$_{14}$-aryloxy)silyl-C$_1$-C$_6$-alkyl, or tris(C$_3$-C$_{10}$-cycloalkoxy) silyl-C$_1$-C$_6$-alkyl, preferably trisethoxysilyl-n-propyl;

R$^5$ represents H;

straight chain or branched, substituted or unsubstituted C$_1$-C$_{14}$-alkyl, preferably C$_1$-C$_8$-alkyl, more preferably methyl, ethyl, n-propyl, i-propyl, n-butyl, i-butyl, or tert.-butyl;

substituted or unsubstituted C$_3$-C$_{10}$-cycloalkyl, preferably C$_5$-C$_8$-cycloalkyl, more preferably cyclopentyl, cyclohexyl or cycloheptyl;

substituted or unsubstituted C$_6$-C$_{14}$-aryl, preferably C$_6$-C$_{10}$-aryl, more preferably phenyl, which aryl group, more preferably phenyl, is either unsubstituted or contains 1, 2, 3, 4 or 5 identical or different substituents, even more preferably 1, 2 or 3 identical or different substituents which are located in the o- and/or p-positions;

R$^6$ represents H, or straight chain or branched, substituted or unsubstituted C$_1$-C$_{14}$-alkyl, preferably C$_1$-C$_8$-alkyl, more preferably methyl, ethyl, n-propyl, i-propyl, n-butyl, i-butyl, or tert.-butyl; or substituted or unsubstituted C$_3$-C$_{10}$-cycloalkyl, preferably C$_5$-C$_8$-cycloalkyl, more preferably cyclopentyl, cyclohexyl or cycloheptyl; or substituted or unsubstituted C$_6$-C$_{14}$-aryl, preferably C$_6$-C$_{10}$-aryl, more preferably phenyl, which aryl group, more preferably phenyl, is either unsubstituted or contains 1, 2, 3, 4 or 5 identical or different substituents; and to yield a compound of general formula (I) wherein R$^1$, R$^2$, R$^3$, R$^4$, R$^5$, R$^6$, M, Y and NHC shall have the same general, preferred and more preferred meanings as outlined above for general formulae (2) and (5).

The General Reaction Scheme of Route 3 is Repeated in the Following:

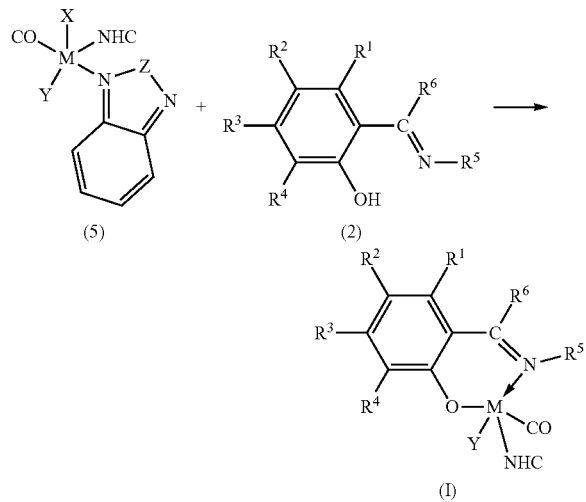

The compound of general formula (5) may be prepared by converting MXY(CO)(PR$_3$)$_3$ wherein M, X, Y, and R having the meaning set forth above with regard to formula (4) with 2,1,3-benzoselenadiazole (BSD) or 2,1,3-benzothiadiazole (BTD) according to the method described in Inorganica Chimica Acta 358, 2005, 3218-26. In particular RuHCl(CO)(PPh$_3$)$_3$ can be reacted with 2,1,3-benzoselenadiazole (BSD) or 2,1,3-benzothiadiazole (BTD) pursuant to the method described in Inorganica Chimica Acta 358, 2005, 3218-26.

Typical and Preferred Compounds (5):

Typical and preferred compounds (5) are those in which X is H, Y is Cl, Z is either S or Se, and NHC is an N-heterocyclic carbene, preferably an N-heterocyclic carbene ligand selected from formulae (IIa) to (IIe) as defined below, more preferably an N-heterocyclic carbene ligand selected from formulae (IIIa) to (IIIu) as defined below.

Typical and Preferred Compounds (2):

The compounds of general formula (2) are the same as defined above for Route 1.

Further Typical Reaction Parameters:

The process according to Route 3 is typically performed in one or more organic solvents, preferably selected from the group consisting of ethers, more preferably THF, dioxane, and diethylether, alkanes, more preferably hexane, aromatic solvents, more preferably toluene, and benzene, halogenated hydrocarbon, more preferably chloroform, dichloromethane and chlorobenzene, ester, more preferably ethyl acetate, ketone, more preferably methyl ethyl ketone, acetone, and alcohols, more preferably methanol, ethanol and methyloxyethanol. Further on the process pursuant to route 3 is beneficial in not requiring any catalyst like Ag$_2$CO$_3$ or TlOEt and allows the preparation of compounds according to general formula (I) in high purity.

Use of the Complexes and Processes for Manufacturing Hydrogenated Compounds:

The novel Ru and Os based complexes of general formula (I) are useful as catalysts, either alone or in combination with suitable co-catalysts or additives, for the hydrogenation of a wide variety of unsaturated organic and polymeric materials. However, is has proven not necessary to add any co-catalysts of additives.

Hence the present invention relates to the use of the complexes of general formula (I) as catalysts for hydrogenation reactions. The present invention also relates to a process for manufacturing partially or fully saturated compounds by contacting unsaturated compounds containing at least one C=C double bond with hydrogen in the presence of at least one compound according to general formula (I).

Substrates to be Hydrogenated:

The process of the present invention is broadly applicable to the hydrogenation of a variety of substrates, including terminal olefins, internal olefins, cyclic olefins, conjugated olefins, and any further olefins having at least one carbon-carbon double bond and additionally at least one further polar unsaturated double or triple bond. The process is also applicable to the hydrogenation of polymers having carbon-carbon double bonds. Such polymers may represent homo-, co- or terpolymers.

As a terminal olefin or alkene, it is possible to hydrogenate a hydrocarbon compound with a terminal unsaturated carbon-carbon double bond having the general formula C$_n$H$_{2n}$. The terminal olefin can be a straight-chain or a branched hydrocarbon compound of any length, preferably 1-hexene.

As an internal olefin or alkene, it is possible to hydrogenate a hydrocarbon compound with an internal unsaturated carbon-carbon double bond having the general formula C$_n$H$_{2n}$. The internal olefin can be a straight-chain or a branched hydrocarbon of any length, preferably 2-hexene.

As a cyclic olefin or cycloalkene, it is possible to hydrogenate a hydrocarbon compound with a cyclic unsaturated carbon-carbon double bond having the general formula $C_nH_{2n-2}$. The cyclic olefin can be a ring of any size, preferably cyclohexene.

As a conjugated olefin or dialkene, it is possible to hydrogenate a hydrocarbon compound with conjugated carbon-carbon unsaturated double bonds. The conjugation can be a straight-chain or a branched hydrocarbon of any length, preferably styrene.

As an olefin, it is also possible to selectively hydrogenate a hydrocarbon compound with at least one unsaturated carbon-carbon double bond and least one other unsaturated polar double or triple bond. Such unsaturated polar bonds are surprisingly left unaltered. The carbon-carbon double bond in such olefins can be of any nature including terminal, internal, cyclic and conjugated ones. The additional unsaturated polar bond can be of any nature with preference given to carbon-nitrogen, carbon-phosphorus, carbon-oxygen, and carbon-sulfur unsaturated polar bonds.

Polymers having carbon-carbon double bonds may also be subjected to the inventive process. Such polymers preferably comprise repeating units based on at least one conjugated diene monomer.

The conjugated diene can be of any nature. In one embodiment $(C_4-C_6)$ conjugated dienes are used. Preference is given to 1,3-butadiene, isoprene, 1-methylbutadiene, 2,3-dimethylbutadiene, piperylene, chloroprene, or mixtures thereof. More preference is given to 1,3-butadiene, isoprene or mixtures thereof. Particular preference is given to 1,3-butadiene.

In a further embodiment polymers having carbon-carbon double bonds may be subjected to the inventive process which comprise repeating units of not only at least one conjugated diene as monomer (a) but additionally at least one further copolymerizable monomer (b).

Examples of suitable monomers (b) are olefins, such as ethylene or propylene.

Further examples of suitable monomers (b) are vinylaromatic monomers, like styrene, α-methyl styrene, o-chlorostyrene or vinyltoluenes, vinylesters of aliphatic or branched $C_1-C_{18}$ monocarboxylic acids, such as vinyl acetate, vinyl propionate, vinyl butyrate, vinyl valerate, vinyl hexanoate, vinyl 2-ethylhexanoate, vinyl decanoate, vinyl laurate and vinyl stearate.

A preferred polymer to be used in the present invention is a copolymer of 1,3-butadiene and styrene or alpha-methylstyrene. Said copolymers may have a random or block type structure.

Further examples of suitable monomers (b) are esters of ethylenically unsaturated monocarboxylic acids or mono- or diesters of dicarboxylic acids with generally $C_1-C_{12}$ alkanols, e.g. esters of acrylic acid, methacrylic acid, maleic acid, fumaric acid and itaconic acid with e.g. methanol, ethanol, n-propanol, isopropanol, 1-butanol, 2-butanol, isobutanol, tert.-butanol, n-hexanol, 2-ethylhexanol, or $C_5-C_{10}$-cycloalkanols, such as cyclopentanol or cyclohexanol, and of these preferably the esters of acrylic and/or methacrylic acid, examples being methyl methacrylate, n-butyl methacrylate, tert-butyl methacrylate, n-butyl acrylate, tert-butyl acrylate, and 2-ethylhexyl acrylate.

Nitrile Rubber:

The inventive process may be further used to hydrogenate so-called nitrile rubbers. Nitrile rubbers (also abbreviated as "NBR") represent copolymers or terpolymers containing repeating units of at least one conjugated diene, at least one α,β-unsaturated nitrile monomer and, if appropriate, one or more further copolymerizable monomers.

The conjugated diene can be of any nature. Preference is given to using $(C_4-C_6)$ conjugated dienes, more preferably selected from the group consisting of 1,3-butadiene, isoprene, 2,3-dimethylbutadiene, piperylene and mixtures thereof. Very particular preference is given to 1,3-butadiene and isoprene or mixtures thereof. Especial preference is given to 1,3-butadiene.

As α,β-unsaturated nitrile, it is possible to use any known α,β-unsaturated nitrile, preferably a $(C_3-C_5)$ α,β-unsaturated nitrile, more preferably selected from the group consisting of acrylonitrile, methacrylonitrile, ethacrylonitrile and mixtures thereof. Particular preference is given to acrylonitrile.

A particularly preferred nitrile rubber used in the process of this invention is thus a copolymer having repeating units derived from acrylonitrile and 1,3-butadiene.

Apart from the conjugated diene and the α,β-unsaturated nitrile, the nitrile rubber may comprise repeating units of one or more further copolymerizable monomers known in the art, e.g. α,β-unsaturated (preferably mono-unsaturated) monocarboxylic acids, their esters and amides, α,β-unsaturated (preferably mono-unsaturated) dicarboxylic acids, their mono-oder diesters, as well as the respective anhydrides or amides of said α,β-unsaturated dicarboxylic acids.

As α,β-unsaturated monocarboxylic acids acrylic acid and methacrylic acid are preferably used.

Esters of α,β-unsaturated monocarboxylic acids may also be used, in particular alkyl esters, alkoxyalkyl esters, aryl esters, cycloalkylesters, cyanoalkyl esters, hydroxyalkyl esters, and fluoroalkyl esters.

As alkyl esters $C_1-C_{18}$ alkyl esters of the α,β-unsaturated monocarboxylic acids are preferably used, more preferably $C_1-C_{18}$ alkyl esters of acrylic acid or methacrylic acid, such as methylacrylate, ethylacrylate, propylacrylate, n-butylacrylate, tert.-butylacrylate, 2-ethyl-hexylacrylate, n-dodecylacrylate, methylmethacrylate, ethylmethacrylate, propylmethacrylate, n-butylmethacrylate, tert.-butylmethacrylate and 2-ethylhexyl-methacrylate.

As alkoxyalkyl esters $C_2-C_{18}$ alkoxyalkyl esters of α,β-unsaturated monocarboxylic acids are preferably used, more preferably alkoxyalkylester of acrylic acid or methacrylic acid such as methoxy methyl(meth)acrylate, methoxy ethyl (meth)acrylate, ethoxyethyl(meth)acrylate and methoxyethyl(meth)acrylate.

It is also possible to use aryl esters, preferably $C_6-C_{14}$-aryl-, more preferably $C_6-C_{10}$-aryl esters and most preferably the aforementioned aryl esters of acrylates and methacrylates.

In another embodiment cycloalkyl esters, preferably $C_5-C_{12}$-, more preferably $C_6-C_{12}$-cyclo-alkyl and most preferably the aforementioned cycloalkyl acrylates and methacrylates are used.

It is also possible to use cyanoalkyl esters, in particular cyanoalkyl acrylates or cyanoalkyl methacrylates, with 2 to 12 C atoms in the cyanoalkyl group, preferably α-cyanoethyl acrylate, β-cyanoethyl acrylate or cyanobutyl methacrylate.

In another embodiment hydroxyalkyl esters are used, in particular hydroxyalkyl acrylates and hydroxyalkyl methacrylates with 1 to 12 C-atoms in the hydroxylalkyl group, preferably 2-hydroxyethyl acrylate, 2-hydroxyethyl methacrylate or 3-hydroxypropyl acrylate.

It is also possible to use fluorobenzyl esters, in particular fluorobenzyl acrylates or fluorobenzyl methacrylates, preferably trifluoroethyl acrylate and tetrafluoropropyl methacrylate. Substituted amino group containing acrylates and methacrylates may also be used like dimethylaminomethyl acrylate and diethylaminoethylacrylate.

Various other esters of the α,β-unsaturated carboxylic acids may also be used, like e.g. polyethyleneglycol(meth) acrylate, polypropyleneglycole(meth)acrylate, glycidyl (meth)acrylate, epoxy(meth)acrylate, N-(2-hydroxyethyl) acrylamide, N-(2-hydroxymethyl)acrylamide or urethane (meth)acrylate.

It is also possible to use mixture of all aforementioned esters of α,β-unsaturated carboxylic acids.

Furthon α,β-unsaturated dicarboxylic acids may be used, preferably maleic acid, fumaric acid, crotonic acid, itaconic acid, citraconic acid and mesaconic acid.

In another embodiment anhydrides of α,β-unsaturated dicarboxylic acids are used, preferably maleic anhydride, itaconic anhydride, itaconic anhydride, citraconic anhydride and mesaconic anhydride.

In a further embodiment mono- or diesters of α,β-unsaturated dicarboxylic acids can be used. Suitable alkyl esters are e.g. $C_1$-$C_{10}$-alkyl, preferably ethyl-, n-propyl-, iso-propyl, n-butyl-, tert.-butyl, n-pentyl-oder n-hexyl mono- or diesters. Suitable alkoxyalkyl esters are $C_2$-$C_{12}$-alkoxyalkyl-, preferably $C_3$-$C_8$-alkoxyalkyl mono- or diesters. Suitable hydroxyalkyl esters are $C_1$-$C_{12}$ hydroxyalkyl-, preferably $C_2$-$C_8$-hydroxyalkyl mono- or diesters. Suitable cycloalkyl esters are $C_5$-$C_{12}$-cycloalkyl-, preferably $C_6$-$C_{12}$-cycloalkyl mono- or diesters. Suitable alkylcycloalkyl esters are $C_6$-$C_{12}$-alkylcycloalkyl-, preferably $C_7$-$C_{10}$-alkylcycloalkyl mono- or diesters. Suitable aryl esters are $C_6$-$C_{14}$-aryl, preferably $C_6$-$C_{10}$-aryl mono- or diesters.

Explicit examples of the α,β-ethylenically unsaturated dicarboxylic acid monoester monomers include
- maleic acid monoalkyl esters, preferably monomethyl maleate, monoethyl maleate, monopropyl maleate, and mono n-butyl maleate;
- maleic acid monocycloalkyl esters, preferably monocyclopentyl maleate, monocyclohexyl maleate, and monocycloheptyl maleate;
- maleic acid monoalkylcycloalkyl esters, preferably monomethylcyclopentyl maleate, and monoethylcyclohexyl maleate;
- maleic acid monoaryl ester, preferably monophenyl maleate;
- maleic acid mono benzyl ester, preferably monobenzyl maleate;
- fumaric acid monoalkyl esters, preferably monomethyl fumarate, monoethyl fumarate, monopropyl fumarate, and mono n-butyl fumarate;
- fumaric acid monocycloalkyl esters, preferably monocyclopentyl fumarate, monocyclohexyl fumarate, and monocycloheptyl fumarate;
- fumaric acid monoalkylcycloalkyl esters, preferably monomethylcyclopentyl fumarate, and monoethylcyclohexyl fumarate;
- fumaric acid monoaryl ester, preferably monophenyl fumarate;
- fumaric acid mono benzyl ester, preferably monobenzyl fumarate;
- citraconic acid monoalkyl esters, preferably monomethyl citraconate, monoethyl citraconate, monopropyl citraconate, and mono n-butyl citraconate;
- citraconic acid monocycloalkyl esters, preferably monocyclopentyl citraconate, monocyclohexyl citraconate, and monocycloheptyl citraconate;
- citraconic acid monoalkylcycloalkyl esters, preferably monomethylcyclopentyl citraconate, and monoethylcyclohexyl citraconate;
- citraconic acid mono aryl ester, preferably monophenyl citraconate;
- citraconic acid mono benzyl ester, preferably monobenzyl citraconate;
- itaconic acid mono alkyl esters, preferably monomethyl itaconate, monoethyl itaconate, monopropyl itaconate, and mono n-butyl itaconate;
- itaconic acid monocycloalkyl esters, preferably monocyclopentyl itaconate, monocyclohexyl itaconate, and monocycloheptyl itaconate;
- itaconic acid monoalkylcycloalkyl esters, preferably monomethylcyclopentyl itaconate, and monoethylcyclohexyl itaconate;
- itaconic acid mono aryl ester, preferably monophenyl itaconate;
- itaconic acid mono benzyl ester, preferably monobenzyl itaconate.

As α,β-ethylenically unsaturated dicarboxylic acid diester monomers the analogous diesters based on the above explicitly mentioned mono ester monomers may be used, wherein, however, the two organic groups linked to the C=O group via the oxygen atom may be identical or different.

As further termonomers vinyl aromatic monomers like styrol, α-methylstyrol and vinylpyridine, as well as non-conjugated dienes like 4-cyanocyclohexene and 4-vinylcyclohexene, as well as alkines like 1- or 2-butine may be used.

Particularly preferred are termonomers chosen from the below depicted formulae:

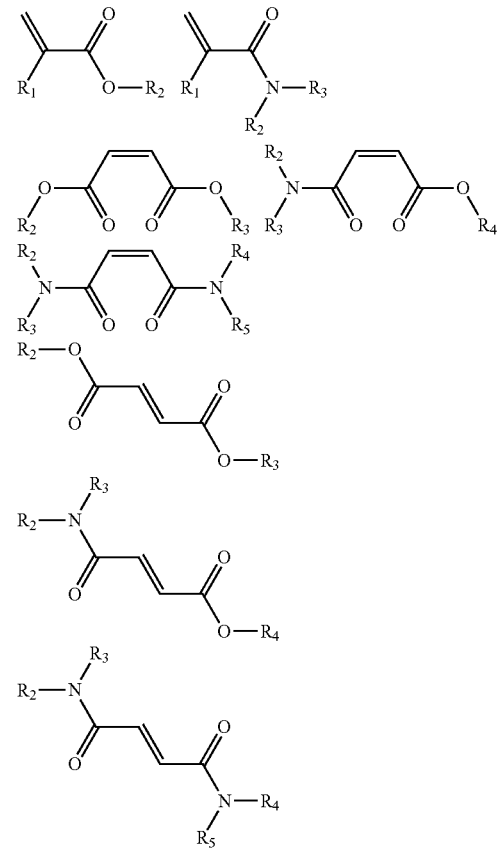

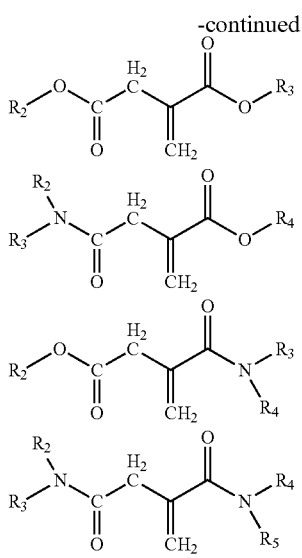

wherein
R¹ is hydrogen or a methyl group, and
R², R³, R⁴, R⁵ are identical or different and may represent H, $C_1$-$C_{12}$ alkyl, $C_3$-$C_8$ cycloalkyl, alkoxyalkyl, hydroxyalkyl, expoxyalkyl, aryl, or heteroaryl.

The proportions of conjugated diene and α,β-unsaturated nitrile in the NBR polymers to be used can vary within wide ranges. The proportion of the conjugated diene or the sum of conjugated dienes is usually in the range from 40 to 90% by weight, preferably in the range from 60 to 85% by weight, based on the total polymer. The proportion of α,β-unsaturated nitrile or the sum of α,β-unsaturated nitriles is usually from 10 to 60% by weight, preferably from 15 to 40% by weight, based on the total polymer. The proportions of the monomers in each case add up to 100% by weight. The additional monomers can be present in amounts of from 0 to 40% by weight, preferably from 0.1 to 40% by weight, particularly preferably from 1 to 30% by weight, based on the total polymer. In this case, corresponding proportions of the conjugated diene or dienes and/or the α,β-unsaturated nitrile or nitriles are replaced by proportions of the additional monomers, with the proportions of all monomers in each case adding up to 100% by weight.

The preparation of the nitrile rubbers by polymerization of the abovementioned monomers is adequately and comprehensively known from prior art. Nitrile rubbers which can be used for the purposes of the invention are also commercially available, e.g. as products from the product range of the Perbunan® and Krynac® grades of Lanxess Deutschland GmbH.

Process Conditions for Hydrogenating the Unsaturated Substrates:

The hydrogenation of the unsaturated substrates, in particular the nitrile rubber can be carried out by bringing the unsaturated substrates, in particular the nitrile rubber, into contact with the novel complex catalyst of general formula (I) in the presence of hydrogen.

The hydrogenation is preferably carried out at a temperature in the range of from 30° C. to 200° C., preferably from 40° C. to 180° C., most preferably from 50° C. to 160° C. and at a hydrogen pressure in the range of 0.5 MPa to 35 MPa, more preferably of 3.0 MPa to 10 MPa.

Preferably, the hydrogenation time is from 10 minutes to 48 hours, preferably from 15 minutes to 24 hours, more preferably from 30 minutes to 4 hours, even more preferably from 1 hour to 8 hours and most preferably from 1 hour to 3 hours.

The amount of the complex catalyst to the unsaturated substrates, in particular the nitrile rubber, depends on the nature and the catalytic activity of the catalyst. The amount of catalyst employed is typically chosen in the range of from 1 to 1000 ppm of noble metal, preferably from 2 to 500 ppm, in particular from 5 to 250 ppm, based on the unsaturated substrates, in particular the nitrile rubber used.

Firstly, a solution of the unsaturated substrates, in particular the nitrile rubber in a suitable solvent is prepared. The concentration of the unsaturated substrates, in particular the nitrile rubber in the hydrogenation reaction is not critical, but it should naturally be ensured that the reaction is not adversely affected by an excessively high viscosity of the reaction mixture and any associated mixing problem. The concentration of the unsaturated substrates, in particular the nitrile rubber in the reaction mixture is preferably in the range from 1 to 25% by weight, particularly preferably in the range from 5 to 20% by weight, based on the total reaction mixture.

The hydrogenation reaction is typically carried out in a suitable solvent which does not deactivate the catalyst used and also does not adversely affect the reaction in any other way. Preferred solvents include but are not restricted to dichloromethane, benzene, toluene, monochlorobenzene, methyl ethyl ketone, acetone, methyl isobutyl ketone, tetrahydrofuran, tetrahydropyran, dioxane and cyclohexane. The particularly preferred solvents are monochlorobenzene, methyl ethyl ketone and acetone.

Such solution of the nitrile rubber is then brought into contact with the catalyst according to general formula (I) in the presence of hydrogen at the pressure mentioned above. The reaction mixture is typically stirred or any kind of shear can be introduced to allow sufficient contact of the solution with the hydrogen phase.

One major advantage of the present invention resides in the fact that the complex catalyst used is very active, so that the catalyst residue in the final HNBR products can be low enough to make the catalyst metal removal or recycle step alleviated or even unnecessary. However, to the extent desired, the catalysts used during the process of the present invention may be removed. Such removal can be performed e.g. by using ion-exchange resins as described in EP-A-2 072 532 A1 and EP-A-2 072 533 A1. The reaction mixture obtained after the completion of the hydrogenation reaction can be taken and treated with an ion-exchange resin at e.g. 100° C. for 48 hours under nitrogen which leads to a bonding of the catalyst to the resin while the reaction mixture can be worked up with the usual finishing methods.

The rubber can then be obtained from the solution by known workup procedures such as steam coagulation, solvent evaporation or precipitation and dried to a degree that allows usage in typical rubber processing methods.

Process for Hydrogenating Diene-Based Polymers Via so-Called Latex-Hydrogenation:

In a further specific embodiment the present invention also relates to a process for selectively hydrogenating the carbon-carbon double bonds in diene-based polymers which polymers are present in latex form, this means as a suspension of diene-based polymer particles in an aqueous medium, by using the novel complex catalyst of general formula (I) in the presence of hydrogen, therefore resulting in a hydrogenated diene-based polymer present in an aqueous suspension. Such process which may also be referred as latex hydrogenation can be achieved with a high degree of hydrogenation.

These latices include both suspensions prepared by free-radical polymerization of aqueous monomer emulsions (primary suspensions) and those whose polymers have been prepared by whatever method or route and are then converted to an aqueous suspension form (secondary suspensions). The term "aqueous suspension" also embraces, in principle, suspensions of microcapsules.

Preferably, according to the present invention, the polymer solid content in the aqueous suspension lies in the range of from 1 to 75% by weight, more preferably from 5 to 30% by weight based on the total weight of the aqueous suspension.

The preparation of such diene-based polymers which may be subjected to the latex hydrogenation process pursuant to this invention is known to the skilled worker and can in principle be carried out by anionic, free-radical or Ziegler-Natta polymerization in solution, in bulk, in suspension or in emulsion. As described above, such polymers contain repeating units of at least one conjugated diene and depending on the type of reaction, the conjugated dienes are 1,4- and/or 1,2 polymerized. For the latex hydrogenation process of the invention it is preferred to employ polymers prepared by free-radical aqueous emulsion polymerization of the above mentioned monomers (a) and (b). These techniques are sufficiently well known to the skilled worker and are described at length in the literature, for example in Ullmann's Encyclopedia of Industrial Chemistry, $5^{th}$ Edition, Volume A 21, pp 373-393. In general such polymers are prepared in the presence of free-radical initiators and, if desired, surface-active substances such as emulsifiers and protective colloids (see for example Houben Weyl, Methoden der organischen Chemie, Volumen XIV/1, Makromolekulare Stoffe, Georg Thieme Verlag, Stuttgart, 1961, pp 192-208).

Suitable free-radical polymerization initiators include organic peroxides, such as tert-butyl hydroperoxide, benzoyl hydroperoxide, diisopropylbenzoyl peroxide, inorganic peroxides, such as hydrogen peroxide, salts of peroxomono and/or peroxodisulfuric acid, especially the ammonium and/or alkali metal peroxodisulfates (persulfates), and azo compounds, particular preference being given to the persulfates. Preference is also given to combined systems composed of at least one organic reducing agent and at least one peroxide and/or hydroperoxide, such as tert-butyl hydroperoxide and the sodium salt of hydroxymethanesulfonic acid, or hydrogen peroxide and ascorbic acid (as an electrolyte-free redox initiator system) and to combine systems which additionally comprise a small amount of a metal compound which is soluble in the polymerization medium and whose metallic component can exist in a plurality of valence states, for example ascorbic acid/iron(II) sulfate/hydrogen peroxide, it also being possible frequently to replace the ascorbic acid by the sodium salt of hydroxymethanesulfinic acid, sodium sulfite, sodium hydrogensulfite or sodium bisulfite and the hydrogen peroxide by tert-butyl hydroperoxid, alkali metal peroxodisulfates and/or ammonium peroxodisulfate. Instead of a water-soluble iron(II) salt it is also possible to employ a combination of water-soluble Fe/V salts.

These polymerization initiators are employed in customary amounts, such as in amounts of from 0.01 to 5, preferably from 0.1 to 2.0% b.w., based on the monomers to be polymerized. The monomer mixtures can, if desired, be polymerized in the presence of customary regulators, such as mercaptans, an example of which is tert.-dodecyl mercaptan.

These regulators are then used in an amount of from 0.01 to 5% b.w., based on the overall amount of the mixture.

There are no particular restrictions on the emulsifiers that can be used. Preference is given to neutral emulsifiers such as ethoxylated mono-, di- and trialkylphenols (ethyleneoxide degree: 3 to 50; Alkyl $C_4$ to $C_9$) or ethoxylated fatty alcohols (ethyleneoxide degree: 3 to 50; alkyl $C_4$ to $C_9$) and/or anionic emulsifiers, such as the alkali metal and ammonium salts of fatty acids (alkyl: $C_{12}$ to $C_{24}$), of alkyl sulfates (alkyl: $C_8$ to $C_{22}$), of sulfuric monoesters of ethoxylated alkanols (ethyleneoxide degree: 4 to 30, alkyl: $C_8$ to $C_{22}$) and of ethoxylated alkylphenols (ethyleneoxide degree: 3 to 50, alkyl: $C_4$ to $C_{20}$), of alkylsulfonic acids (alkyl: $C_8$ to $C_{22}$) and of alkylarylsulfonic acids (alkyl: $C_4$ to $C_{18}$). Further suitable anionic emulsifiers are alkali metal or ammonium salts of mono- or di-$C_{4-24}$ alkyl derivatives of bis(phenylsulfonic acid)ether.

Particular preference is given to the alkali metal and/or ammonium salts, especially the sodium salts, of alkylarylsulfonic acids, alkylsulfonic acids (eg. sulfonated $C_{12}$-$C_{18}$ paraffin), alkylsulfates (eg. sodium lauryl sulfonate) and of the sulphuric monoesters of ethoxylated alkanols (eg. sulfoxylated ethoxylate of lauryl alcohol with 2 to 3 ethyleneoxide units). Further suitable emulsifiers are the sodium or potassium salts of fatty acids ($C_{12}$-$C_{23}$-alkyl radicals), such as potassium oleate. Additional appropriate emulsifiers are given in Houben-Weyl, loc. Cit., pp. 192-208. Instead of or in a mixture with emulsifiers it is also possible, however, to employ conventional protective colloids, such as polyvinyl alcohol, polyvinylpyrrolidone or amphiphilic block polymers with short hydrophobic blocks, for the purpose of co-stabilization. In general the amount of emulsifiers used, based on the monomers to be polymerized, will not exceed 5% by weight.

The free-radical polymerization reaction can be carried out by the whole-batch initial charge (batch) technique, but is preferably operated, especially on the industrial scale, in accordance with the feed technique. In this latter technique the major amount (generally from 50 to 100% by weight) of the monomers to be polymerized are added to the polymerization vessel in accordance with the progress of the polymerization of the monomers already in the polymerization vessel. In this context; the free-radical initiator system can be either included entirely in the initial charge to the polymerization vessel or else added continuously or in stages to the polymerization reaction at the rate at which it is consumed in the course of the free-radical aqueous emulsion polymerization. In each individual case this will depend, as is known, both on the chemical nature of the initiator system and on the polymerization temperature. The initiator system is preferably supplied to the polymerization zone at the rate at which it is consumed.

The polymerization reaction may also be conducted in the presence of an aqueous polymer suspension as polymer seed latex. Such techniques are generally known to the skilled worker and are described e.g. in DE-A 42 13 967, DE-A 42 13 968, EP-A 567 811, EP 567 812 or EP 567 819. In principle it is possible depending on the desired character, to include the seed in the initial charge or to add it continuously or in stages in the course of polymerization. The polymerization is preferably carried out with the seed in the initial charge. The amount of seed polymer is preferably in the range from 0.05 to 5% by weight, preferably from 0.1 to 2% by weight and, in particular, from 0.2 to 1% by weight, based on the monomers a) to d). The polymer particles of the seed latex that is used preferably have weight-average diameters in the range from 10 to 100 nm, preferably fro 20 to 60 nm and in particular, about 30 nm. Preference is given to the use of a polystyrene seed.

The polymerization reaction is preferably carried out above atmospheric pressure. The polymerization time can vary within a wide range, and is generally from 1 to 15 hours, preferably from 3 to 10 hours. The temperature of polymerization is also variable a wide range and, depending on the initiator used, is from about 0 to 110° C.

The polymer suspensions prepared in this way generally have solid contents of up to 75% by weight. For use in the hydrogenation process of the invention it is possible to employ the suspensions with these solid contents. In some cases, however, it is advisable to dilute the suspensions to an appropriate solid content beforehand. The solid content of the suspensions employed is preferably in the range from 5 to 30% by weight, based on the overall weight of suspension.

The surface-active substances still present, in general, in the polymer suspensions, and further substances used, for example, as customary polymerization auxiliaries in emulsion polymerizations, do not have a disruptive effect on the hydrogenation process of the invention. However, it may be advisable to subject the polymer suspensions to chemical or physical deodorization before hydrogenation. Physical deodorization, by stripping the residual monomers with steam, is known, for example, from EP-A 584 458. EP-A 327 006 for its part recommends the use of conventional distillation methods. Chemical deodorization takes place preferably by means of a post polymerization following the main polymerization. Such processes are described, for example, in DE-A 383 4734, EP-A 379 892, EP-A 327 006, DE-A 44 19 518, DE-A 44 35 422 and DE-A 44 35 423.

In a preferred embodiment a hydrogenation of a nitrile rubber latex is preferably carried out at a temperature in the range of from 30° C. to 150° C. under hydrogen pressure, preferably from 40° C. to 140° C., most preferably from 50° C. to 130° C. and at a hydrogen pressure in the range of 0.5 MPa to 35 MPa, more preferably of 3.0 MPa to 10 MPa.

Preferably, the hydrogenation time is from 10 minutes to 48 hours, preferably from 15 minutes to 36 hours, more preferably from 30 minutes to 24 hours, even more preferably from 1 hour to 20 hours and most preferably from 1 hour to 18 hours.

The amount of the complex catalyst to the unsaturated substrates, in particular the nitrile rubber, depends on the nature and the catalytic activity of the catalyst. The amount of catalyst employed is typically chosen in the range of from 1 to 1000 ppm of noble metal, preferably from 2 to 500 ppm, in particular from 5 to 250 ppm, based on the unsaturated substrates, in particular the nitrile rubber in the latex form.

For the purposes of the present invention, hydrogenation is a reaction of the double bonds present in the unsaturated substrates, in particular the nitrile rubber to an extent of at least 50%, preferably 70-100%, more preferably 80-100%, even more preferably 90-100% and most preferably 95-100%.

After the completion of the hydrogenation according to the present invention a hydrogenated nitrile rubber having a Mooney viscosity (ML1+4 at 100° C.), measured in accordance with ASTM standard D 1646, in the range from 1 to 130, preferably from 10 to 100, is obtained. This corresponds to a weight average molecular weight Mw in the range 2,000-400,000 g/mol, preferably in the range 20,000-200,000. The hydrogenated nitrile rubbers obtained also have a polydispersity PDI=Mw/Mn, where Mw is the weight average molecular weight and Mn is the number average molecular weight, in the range 1-5 and preferably in the range 2-4.

The invention is further illustrated but is not intended to be limited by the following examples in which all parts and percentages are by weight unless otherwise specified.

EXAMPLES

Abbreviations
phr per hundred rubber (weight)
rpm revolution per minute
HD hydrogenation degree
Mn number-average molecular weight
Mw weight-average molecular weight
PDI polydispersity index, defined as Mw/Mn
$PPh_3$ triphenylphosphine
MCB monochlorobenzene
Rt. room temperature (22+/−2° C.)
RDB residue double bonds, in %, RDB=(1-hydrogenation degree)*100% with NBR having an RDB of 100%
NHC N-heterocyclic-carbene
Cy cyclohexyl
IMes N,N'-bis(mesityl)imidazol-2-ylidene
SIMes N,N'-bis(mesityl)imidazolidin-2-ylidene, also can be called H2-Imes
IPr N,N'-bis(2,6-diisopropylphenyl)imidazol-2-ylidene
ItBu N,N'-bis(tert-butyl)imidazol-2-ylidene
1. Preparation of Catalysts Pursuant to Route 1
1.1 Complex (3a)-$PCy_3$

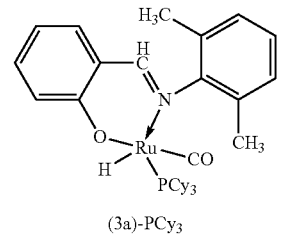

(3a)-$PCy_3$

Complex (3a)-$PCy_3$ is prepared from complex RuHCl(CO)($PCy_3$)$_2$ as follows: 6.0 g of RuHCl(CO)($PCy_3$)$_2$, 1.86 g of compound (2a) and 1.14 g of $Ag_2CO_3$ were dissolved in 80 mL of anhydrous tetrahydrofuran (THF). After stirring the solution at 40° C. for 72 hours, the solution was cooled to 0° C. and filtrated. The filtrate was collected in a schlenk flask, and the solvent was removed under vacuum. 5 mL hexane were added to the brown residue, and the suspension was filtrated. The precipitate was washed three times with 5 mL of anhydrous hexane. After drying, 3.87 grams of yellow solid was obtained. The yield was 73.8%. The reaction was completely conducted under inert gas protection.
1.2 Complex (Ia)-IMes

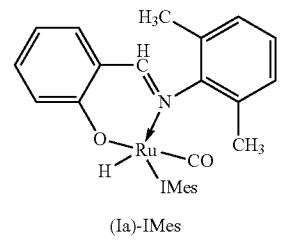

(Ia)-IMes

Complex (Ia)-IMes is prepared from complex (3a)-PCy$_3$ as follows:

200 mg of complex (3a)-PCy$_3$ and 144 mg of IMes were dissolved in 15 mL of anhydrous hexane and the solution was stirred at 50° C. for 17 hours. Afterwards the solution was cooled to room temperature. The obtained precipitate was filtered washed three times with 3 mL of anhydrous hexane. After drying, 90 mg of yellow solid was obtained. The yield was 43.3%. The reaction was completely conducted under inert gas protection.

1.3 Complex (Ia)-SIMes

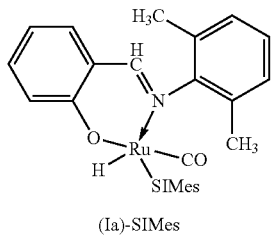

(Ia)-SIMes

Complex (Ia)-SIMes is prepared from complex (3a)-PCy$_3$ as follows:

2 grams of complex (3a)-PCy$_3$ and 1.45 grams of SIMes were dissolved in 100 mL of anhydrous hexane and the solution was stirred at 50° C. for 17 hours. Afterwards the solution was cooled to room temperature and the obtained precipitate was filtered and washed three times with 3 mL hexane. After drying, 1.72 grams of yellow solid was obtained. The yield was 82.7%. The reaction was completely conducted under inert gas protection.

1.4. Complex (Ia)-IPr

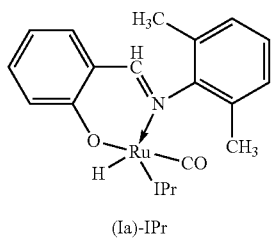

(Ia)-IPr

Complex (Ia)-IPr was prepared from complex (3a)-PCy$_3$ as follows:

200 mg of complex (3a)-PCy$_3$ and 183 mg of IPr were dissolved in 15 mL of anhydrous hexane and the solution was stirred at 50° C. for 17 hours. Afterwards the solution was cooled to room temperature and the obtained precipitate was filtrated and washed three times with 3 mL hexane. After drying, 160 mg of yellow solid was obtained. The yield was 69.8%. The reaction was completely conducted under inert gas protection.

1.5 Complex (3b)-PCy$_3$

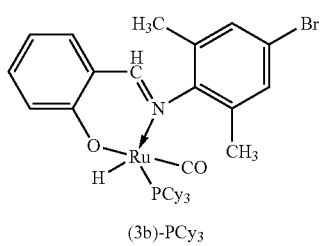

(3b)-PCy$_3$

Complex (3b)-PCy$_3$ is prepared from complex RuHCl(CO)(PCy$_3$)$_2$ as follows:

1.37 grams of RuHCl(CO)(PCy$_3$)$_2$, 0.57 grams of compound (2b) and 0.26 grams of Ag$_2$CO$_3$ were dissolved in 40 mL of anhydrous tetrahydrofuran (THF). After stirred at 40° C. for 72 hours, the solution was cooled to 0° C. and filtrated. The filtrate was collected in a schlenk flask, and the solvent was removed under vacuum. The brown residue was add 5 mL hexane, and the suspension was filtrated. The precipitate was washed three times with 5 mL anhydrous hexane. After drying, 0.45 grams of yellow solid was obtained. The yield was 33.5%. The reaction was completely conducted under inert gas protection.

1.6 Complex (Ib)-IMes

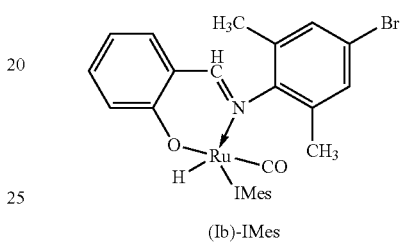

(Ib)-IMes

Complex (Ib)-IMes was prepared from complex (3b)-PCy$_3$ as follows:

200 mg of complex (3b)-PCy$_3$ and 124 mg of IMes were dissolved in 15 mL of anhydrous hexane and the solution was stirred at 50° C. for 18 hours. Afterwards the solution was cooled to room temperature and the obtained precipitate was filtered and washed three times with 3 mL hexane. After drying, 140 mg of yellow solid was obtained. The yield was 67.8%. The reaction was completely conducted under inert gas protection.

1.7 Complex (Ib)-SIMes

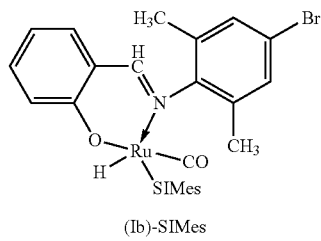

(Ib)-SIMes

Complex (Ib)-SIMes was prepared from complex (3b)-PCy$_3$ as follows:

170 mg of complex (3b)-PCy$_3$ and 107 mg of SIMes were dissolved in 13 mL of anhydrous hexane and the solution was stirred at 50° C. for 18 hours. Afterwards the solution was cooled to room temperature and the obtained precipitate was filtered and washed three times with 3 mL hexane. After drying, 120 mg of yellow solid was obtained. The yield was 68.0%. The reaction was completely conducted under inert gas protection.

1.8 Complex (Ib)-IPr

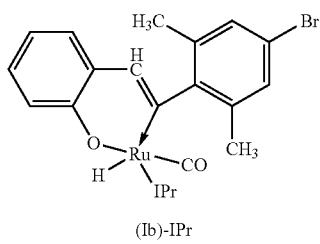

(Ib)-IPr

Complex (Ib)-IPr was prepared from complex (3b)-PCy3 as follows:

200 mg of complex (3b)-PCy$_3$ and 160 mg of IPr were dissolved in 15 mL of anhydrous hexane and the solution was stirred at 50° C. for 17 hours. Afterwards the solution was cooled to room temperature and the obtained precipitate was filtered and washed three times with 3 mL hexane. After drying, 90 mg of yellow solid was obtained. The yield was 40.4%. The reaction was completely conducted under inert gas protection.

1.9 Complex (3c)-PCy$_3$

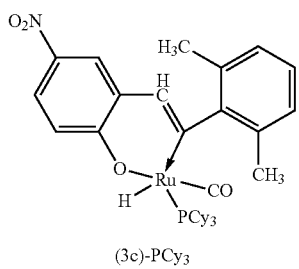

(3c)-PCy$_3$

Complex (3c)-PCy$_3$ is prepared from complex RuHCl(CO)(PCy$_3$)$_2$ as follows:

2.0 g of RuHCl(CO)(PCy$_3$)$_2$, 0.76 g of compound (2c) and 0.38 g of Ag$_2$CO$_3$ were dissolved in 50 mL of anhydrous tetrahydrofuran (THF). After stirred at 40° C. for 72 hours, the solution was cooled to 0° C. and filtrated. The filtrate was collected in a schlenk flask, and the solvent was removed under vacuum. The brown residue was add 5 mL hexane, and the suspension was filtrated. The precipitate was washed two times with 1 mL anhydrous hexane and two times with 1 mL anhydrous toluene. After drying, 1.20 g of brown solid was obtained. The yield was 64.2%. The reaction was completely conducted under inert gas protection.

1.10 Complex (Ic)-IMes

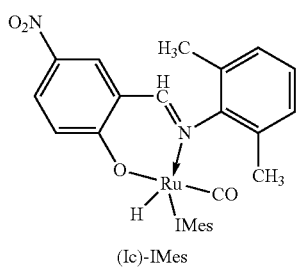

(Ic)-IMes

Complex (Ic)-IMes was prepared from complex (3c)-PCy$_3$.

200 mg of complex (3c)-PCy$_3$ and 133 mg of IMes were dissolved in 20 mL of anhydrous hexane and the solution was stirred at 50° C. for 17 hours. Afterwards the solution was cooled to room temperature and the obtained precipitate was filtered and washed three times with 3 mL hexane. After drying, 200 mg of yellow solid was obtained. The yield was 96%. The reaction was completely conducted under inert gas protection.

1.11 Complex (Ic)-SIMes

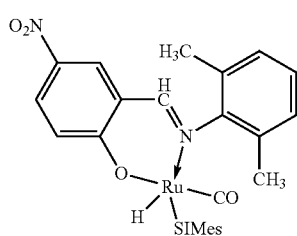

(Ic)-SIMes

Complex (Ic)-SIMes was prepared from complex (3c)-PCy$_3$ as follows:

200 mg of complex (3c)-PCy$_3$ and 135 mg of SIMes were dissolved in 15 mL of anhydrous hexane and the solution was stirred at 50° C. for 17 hours. Afterwards the solution was cooled to room temperature and the obtained precipitate was filtered and washed three times with 3 mL hexane. After drying, 150 mg of yellow solid was obtained. The yield was 71%. The reaction was completely conducted under inert gas protection.

1.12 Complex (3b)-PPh$_3$

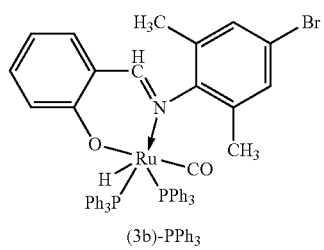

(3b)-PPh$_3$

Complex (3b)-PPh$_3$ was prepared from complex RuHCl(CO)(PPh$_3$)$_3$ as follows:

200 g of RuHCl(CO)(PPh$_3$)$_3$, 64 g of compound (2b) and 28.8 g of Ag$_2$CO$_3$ were dissolved in 10 mL of anhydrous tetrahydrofuran (THF). After stirred at 40° C. for 72 hours, the solution was cooled to 0° C. and filtrated. The brown filter residue was dissolved in 1.5 mL toluene. Subsequently 4 mL hexane was added to precipitate the unreacted raw material. Then filtrated and the collected filtration was cooled to −70° C. to precipitate the yellow product. The product was washed three times with 5 mL anhydrous hexane. After drying, 30 mg of yellow solid was obtained. The yield was 15%. The reaction was completely conducted under inert gas protection.

1.13 Complex (3b)-PPh₃

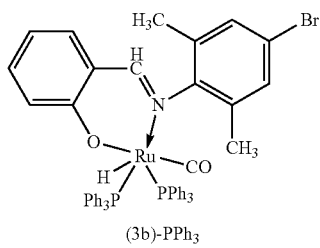

(3b)-PPh₃

Complex (3b)-PPh₃ was prepared from complex RuH₂(CO)(PPh₃)₃ as follows:

50 mg of RuH₂(CO)(PPh₃)₃, and 20 mg of compound (2b) were dissolved in 10 mL of anhydrous toluene. After refluxed for 24 hours, the solution was cooled to 0° C. and filtrated. The brown filter residue was dissolved in 1.5 mL toluene. Subsequently 4 mL hexane was added to precipitate the unreacted raw material. Then filtrated and the collected filtration was cooled to −70° C. to precipitate the yellow product. The product was washed with anhydrous hexane (5 mL*3). After drying, 21 mg of yellow solid was obtained. The yield was 42%. All the operation was conducted under inert gas protection.

1.14 Complex (Ib)-SIMes

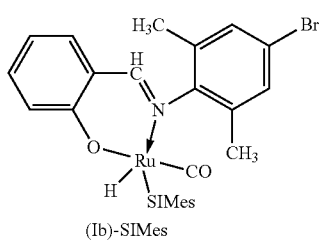

(Ib)-SIMes

Complex (Ib)-SIMes was prepared from complex (3b)-PPh₃ as follows:

25 mg of complex (3b)-PPh₃ and 13 mg of SIMes were dissolved in 4 mL of anhydrous THF and the solution was stirred at 23° C. for 3 hours. Afterwards the solution was removed under vacuum. Then 0.5 mL hexane was added to precipitate the yellow solid. The obtained precipitate was filtrated and washed two times with 0.5 mL hexane. After drying, 10 mg of yellow solid was obtained. The yield was 52%. The reaction was completely conducted under inert gas protection.

2. Preparation of Catalysts Pursuant to Route 2

2.1 Complex (Ia)-IMes

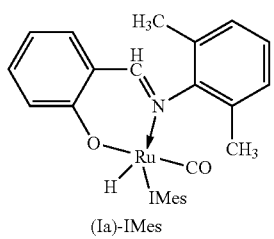

(Ia)-IMes 200 mg of RuHCl(CO)(PCy₃)(IMes), 60 mg of compound (2a) and 37 mg of Ag₂CO₃ were dissolved in 8 mL of anhydrous tetrahydrofuran (THF). After stirred at 40° C. for 72 hours, the solution was cooled to 0° C. and filtrated. The filtrate was collected in a Schlenk flask, and the solvent was removed under vacuum. The brown residue was dissolved in 1 mL toluene and then precipitated in 1 mL hexane. Then the suspension was filtrated again. The filtrate residue was washed two times with 1 mL hexane and two time with 1 mL toluene. After drying, 80 mg of yellow solid was obtained. The yield was 44%. All the operation was conducted under inert gas protection.

2.2 Complex (Ia)-SIMes

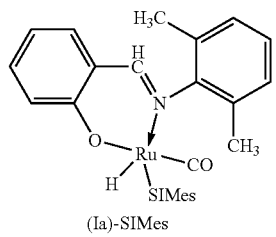

(Ia)-SIMes 200 mg of RuHCl(CO)(PPh₃)(SIMes), 62 mg of compound (2a) and 38 mg of Ag₂CO₃ were dissolved in 8 mL of anhydrous tetrahydrofuran (THF). After stirred at 40° C. for 72 hours, the solution was cooled to 0° C. and filtrated. The filtrate was collected in a Schlenk flask, and the solvent was removed under vacuum. The brown residue was dissolved in 1 mL toluene and then precipitated in 1 mL hexane. Then the suspension was filtrated again. The filtrate residue was washed two times with 1.5 mL hexane. After drying, the product could be obtained. All the operation was conducted under inert gas protection.

3. Characterization of the Complexes Via FT-IR, ¹H-NMR and Single Crystal XRD Analysis Complexes Prepared According to Route 1:

| Complex | CO peak on FT-IR spectrum/cm$^{-1}$ | Proton signal of Ru—H on $^1$H NMR spectrum/ppm |
|---|---|---|
| (3a)-PCy₃ | 1913 | −22.49, −22.54(d) |
| (Ia)-IMes | 1903 | −23.11(s) |
| (Ia)-SIMes | 1903 | −23.21(s) |
| (Ia)-IPr | 1909 | −23.25(s) |
| (3b)-PCy₃ | 1913 | −22.51, −22.57(d) |
| (Ib)-IMes | 1904 | −23.13(s) |
| (Ib)-SIMes | 1907 | −23.23(s) |
| (Ib)-IPr | 1909 | −23.24(s) |
| (3c)-PCy₃ | 1922 | −22.97, −23.02(d) |
| (Ic)-IMes | 1905 | −23.61(s) |
| (Ic)-SIMes | 1907 | −23.65(s) |
| (3b)-PPh₃ | 1917 | −11.30, −11.35, −11.40(t) |
| (Ib)-SIMes | 1908 | −23.23(s) |

Complexes Prepared According to Route 2:

| Complex | CO peak on FT-IR spectrum/cm$^{-1}$ | Proton signal of Ru—H on $^1$H NMR spectrum/ppm |
|---|---|---|
| RuHCl(CO)(PCy₃)(IMes) | 1893 | −24.78, −24.82(d) |
| (Ia)-IMes | 1903 | −23.11(s) |
| RuHCl(CO)(PPh₃)(SIMes) | 1918 | −23.96, −24.01(d) |
| (Ia)-SIMes | 1908 | −23.23(s) |

Single Crystal XRD Analysis of (Ia)-SIMes

A single crystal suitable for XRD measurements was obtained by slow diffusion of diethyl ether into a saturated solution of (Ia)-SIMes in dichloromethane. Data were collected on the Bruker SMART APEX II diffractometer revealing the structure of (Ia)-SIMes depicted in FIG. 4.

4. Hydrogenation Experiments
4.1 Catalysts

The following complex catalysts were used for the hydrogenation of unsaturated substances:
(i) RhCl(PPh$_3$)$_3$ (used in comparative example)
  RhCl(PPh$_3$)$_3$ was purchased from Sigma-Aldrich and used without further purification.
(ii) Complex (3a)-PCy$_3$ (used in comparative example)
  Complex (3a)-PCy$_3$ was prepared as described in Section 1.1.
(iii) Complexes (Ia)-IMes, (Ia)-SIMes, (Ia)-IPr, (Ib)-IMes, (Ib)-SIMes and (Ib)-IPr (used in inventive examples)
  Complexes (Ia)-IMes, (Ia)-SIMes, (Ia)-IPr, (Ib)-IMes, (Ib)-SIMes and (Ib)-IPr were prepared as described in Section 1.

4.2 Nitrile Butadiene Rubbers

The nitrile butadiene rubbers shown in the below Table 1 as used in the examples are all commercially available from Lanxess Deutschland GmbH and had the properties given in Table 1.

TABLE 1

Nitrile butadiene rubbers used in the Examples

| NBR | Acrylonitrile content % by weight | Mooney viscosity ML 1 + 4@100° C. | Mn | Mw | PDI |
|---|---|---|---|---|---|
| Perbunan ® 3431 F | 35 | 28.8 | 76,612 | 257,771 | 3.36 |
| Krynac ® X740 | 27 | 36.0 | 81,020 | 236,370 | 2.86 |
| Krynac ® 4450F | 44 | 42.0 | 81,506 | 232,840 | 2.92 |
| Krynac ® 3330F | 33 | 29.0 | 86,175 | 242,022 | 2.80 |

4.3 Analysis and Test Methods
Measurement of Molecular Weights $M_n$ and $M_w$ by GPC:

The molecular weights $M_n$ and $M_w$ were determined by a Waters GPC system equipped with a Waters 1515 high performance liquid chromatography pump, a Waters 717plus autosampler, a PL gel 10 μm mixed B column and a Waters 2414 RI detector. The GPC test was carried out at 40° C. at 1 mL/min of flow rate with THF as the eluent, and the GPC column was calibrated with narrow PS standard samples.

Measurement of the Hydrogenation Degree by FT-IR:

The spectrum of nitrile rubber before, during and after the hydrogenation reaction was recorded on a Perkin Elmer spectrum 100 FT-IR spectrometer. The solution of the (hydrogenated) nitrile butadiene rubber in MCB was cast onto a KBr disk and dried to form a film for the test. The hydrogenation degree was determined by the FT-IR analysis according to the ASTM D 5670-95 method. The residue double bonds, RDB, can be calculated to be (1-hydrogenation degree)*100%.

Measurement of the Gel Content:

A certain and constant weight of the HNBR sample was dissolved in 20 mL of methylethylketone. The solution was centrifuged for 1 hour at 20,000 rpm. The liquid was decanted and the obtained gel was dried and weight to give the gel content value.

Measurement of the Hydrogenation Degree (HD) and the Residue Double Bonds ("RDB"):

The hydrogenation degree was calculated through $^1$H NMR spectra and the RDB values were calculated through FT-IR spectra.

4.4 Hydrogenation Experiments

Example 1

Hydrogenation of 2-pentene 15 g 2-pentene were dissolved in 235 g of MCB in a 600 mL autoclave. The solution was bubbled with nitrogen for 20 minutes and heated to 130° C. Complex (Ia)-SIMes was dissolved in 15 mL of degassed MCB and the complex solution was injected into the autoclave. Subsequently hydrogen gas was introduced into the autoclave up to the desired pressure. After 5 hours of reaction, the hydrogenation degree reached 99+%.

Example 2

Hydrogenation of 1-tetradecene 300 mL 1-tetradecene were charged in a 600 mL autoclave. The liquid was bubbled with nitrogen for 20 minutes and heated to 130° C. Complex (Ia)-SIMes was dissolved in 15 mL of degassed MCB and the complex solution was injected in to the autoclave. Subsequently the hydrogen gas was introduced into the autoclave up to the desired pressure. After 5 hours of reaction, the hydrogenation degree reached 68%.

The reaction conditions and results of Examples 1 and 2 are summarized in Table 2.

TABLE 2

Examples 1 and 2

| | | Catalyst solution | | Hydrogenation conditions | | | | |
|---|---|---|---|---|---|---|---|---|
| | | (Ia)-SIMes | MCB | $H_2$ | Agitation | Temp | Time | HD |
| Ex. | Substrate | [mg] | [mL] | [MPa] | [rpm] | [° C.] | [hrs] | [%] |
| 1 | 15 g 2-pentene in 235 g MCB | 10 | 15 | 0.84 | 800 | 130 | 5 | 99+ |
| 2 | 300 ml 1-tetradecene | 10 | 15 | 0.84 | 800 | 130 | 5 | 68 |

Comparison Example 1 (CEx1)

Hydrogenation of Perbunan® 3431F; Wilkinson/PPh$_3$ 36 g Perbunan® 3431F were dissolved in 248 g MCB to form a 12 wt % of NBR solution. The solution was filled into an autoclave (600 mL volume) and bubbled with nitrogen gas for 20 minutes to remove dissolved oxygen. Under nitrogen protection, 21.6 mg (0.06 phr) of Wilkinson's catalyst (RhCl(PPh$_3$)$_3$) and 360 mg of PPh$_3$ were dissolved in 15 mL degassed MCB. After the autoclave was heated to 138° C., the catalyst solution was shot into the autoclave. Then the hydrogen was introduced into the autoclave and the pressure was raised to 8.4 MPa. Samples were taken out at intervals for FT-IR test to monitor the RDB. After the finish of NBR hydrogenation, the solution was cooled down and the pressure was released. Then the HNBR solution was treated with thiourea resin to remove Rh metal before stripping. Finally the HNBR crumbs were isolated by stripping and dried in vacuo.

Comparison Example 2 (CEx2)

Hydrogenation of Perbunan® 3431F; Catalyst (3a)-PCy$_3$

The procedure and conditions were the same as in CEx. 1 except that the catalyst was (3a)-PCy$_3$ and its dosage was 10.8 mg (0.03 phr). No co-catalyst PPh$_3$ was used. After the finish of NBR hydrogenation, the HNBR crumbs were directly isolated by stripping and dried in vacuo. The remnant Ru metal was not removed.

Example 3 (Ex3)

Hydrogenation of Perbunan® 3431F; Catalyst (Ia)-IMes

The procedure and conditions were the same as in CEx. 2 except that catalyst (Ia)-IMes was used as inventive catalyst and that its dosage was 10.8 mg (0.03 phr).

Example 4 (Ex4)

Hydrogenation of Perbunan® 3431F; Catalyst (Ia)-SIMes

The procedure and conditions were the same as in CEx. 2 except that catalyst (Ia)-SIMes was used as inventive catalyst and that its dosage was 10.8 mg (0.03 phr).

Example 5 (Ex5)

Hydrogenation of Perbunan® 3431F; Catalyst (Ia)-IPr

The procedure and conditions were the same as in CEx. 2 except that catalyst (Ia)-IPr was used as inventive catalyst and that its dosage was 10.8 mg (0.03 phr).

Example 6 (Ex6)

Hydrogenation of Perbunan® 3431F; Catalyst (Ib)-IMes

The procedure and conditions were the same as in CEx. 2 except that catalyst (Ib)-IMes was used as inventive catalyst and that its dosage was 10.8 mg (0.03 phr).

Example 7 (Ex. 7)

Hydrogenation of Perbunan® 3431F; Catalyst (Ib)-SIMes

The procedure and conditions were the same as in CEx. 2 except that catalyst (Ib)-SIMes was used as inventive catalyst and that its dosage was 10.8 mg (0.03 phr).

Example 8 (Ex. 8)

Hydrogenation of Perbunan® 3431F; Catalyst (Ib)-IPr

The procedure and conditions were the same as in CEx. 2 except that catalyst (Ib)-IPr was used as inventive catalyst and that its dosage was 10.8 mg (0.03 phr). The RDB depending on the hydrogenation time for Examples 1 to 8 is shown in FIG. 1.

Example 9 (Ex. 9)

Hydrogenation of Perbunan® 3431F; Catalyst (Ia)-SIMes at 80° C.

The procedure and conditions were the same as in Ex. 4 except that the hydrogenation was conducted at 80° C.

Example 10 (Ex. 10)

Hydrogenation of Perbunan® 3431F; Catalyst (Ia)-IMes at 65° C.

The procedure and conditions were the same as in Ex. 4 except that the hydrogenation was conducted at 65° C.

Example 11 (Ex. 11)

Hydrogenation of Perbunan® 3431F; Catalyst (Ia)-SIMes at 50° C.

The procedure and conditions were the same as in Ex. 4 except that the hydrogenation was conducted at 50° C. The RDB depending on the hydrogenation time for Examples 4, and 9 to 11 is shown in FIG. 2.

Example 12 (Ex. 12)

Hydrogenation of Perbunan® 3431F; Catalyst (Ia)-SIMes with 0.015 Phr Loading

The procedure and conditions were the same as in Ex. 4 except that the dosage of catalyst (Ia)-SIMes was 5.4 mg (0.015 phr). The RDB depending on the hydrogenation time for Examples 4 and 12 is shown in FIG. 3.

Example 13 (Ex. 13)

Hydrogenation of Krynac® X740; Catalyst (Ia)-SIMes

The procedure and conditions were the same as in Ex. 4 except that the NBR feedstock was Krynac® X740. The concentration of NBR was decreased from 12 wt % to 6 wt %. The dosage of catalyst (Ia)-SIMes was 0.06 phr.

Example 14 (Ex. 14)

Hydrogenation of Krynac® 4450F; Catalyst (Ia)-SIMes

The procedure and conditions were the same as in Ex. 4 except that Krynac® 4450F was hydrogenated.

Example 15 (Ex. 15)

Hydrogenation of Krynac® 3330F; Catalyst (Ia)-SIMes

The procedure and conditions were the same as in Ex. 4 except that Krynac® 3330F was hydrogenated.

The conditions and results of the hydrogenation reactions are summarized in the following Tables 3 to 5.

TABLE 3

Molecular weights and PDI of the hydrogenated nitrile rubber after the hydrogenation time indicated in Table 3 (starting material in all listed examples: Perbunan 3431F with Mn = 76,612, Mw = 257,771; PDI = 3.36)

| Example | Mn | Mw | PDI |
| --- | --- | --- | --- |
| CEx. 1 | 94,953 | 265,278 | 2.79 |
| Ex. 3 | 105,365 | 309,760 | 2.94 |
| Ex. 4 | 99,648 | 286,372 | 2.87 |
| Ex. 5 | 101,159 | 307,925 | 3.04 |
| Ex. 7 | 98,184 | 290,929 | 2.96 |

TABLE 4

Mooney viscosity ML 1 + 4@100° C.
of the hydrogenated nitrile rubber of Examples
3, 4, and 6 after the hydrogenation time indicated in Table 3

| Example | ML(1 + 4)@100° C. |
|---------|-------------------|
| Ex. 3   | 81.2              |
| Ex. 4   | 69                |
| Ex. 6   | 73                |

It can be easily seen from Table 5 that the novel catalysts allow a remarkable reduction of the hydrogenation temperature. Even at temperatures of only 80° C. or 65° C. (Examples 8 and 9) the RDB values are as good as at a reaction temperature of 138° C. used in the other examples after the same reaction times. Even with a hydrogenation temperature of 50° C. a RDB of 0.8 can be achieved after 23 hours.

TABLE 5

Hydrogenation conditions and results for CEx. 1 and CEx.2 and Ex. 3 to 15

| | NBR solution | | Catalyst and solvent | | | Hydrogenation conditions | | | | |
|---|---|---|---|---|---|---|---|---|---|---|
| | Nitrile | MCB | Complex catalyst | | MCB | $H_2$ | Agitation | Temp | Time | RDB* |
| No | rubber [g] | [g] | Type | Weight [mg] | [mL] | [MPa] | [rpm] | [° C.] | [hrs] | [%] |
| CEx. 1 | 36 | 248 | Wilkinson/PPh₃ | 21.6/360 | 15 | 8.4 MPa | 800 rpm | 138 | 3.5 | 11.9 |
| CEx. 2 | 36 | 248 | (3a)-PCy₃ | 10.8 | 15 | 8.4 MPa | 800 rpm | 138 | 3 | 45.1 |
| Ex. 3 | 36 | 248 | (Ia)-IMes | 10.8 | 15 | 8.4 MPa | 800 rpm | 138 | 3 | 0.7 |
| Ex. 4 | 36 | 248 | (Ia)-SIMes | 10.8 | 15 | 8.4 MPa | 800 rpm | 138 | 2 | 1.7 |
| Ex. 5 | 36 | 248 | (Ia)-IPr | 10.8 | 15 | 8.4 MPa | 800 rpm | 138 | 3 | 1.9 |
| Ex. 6 | 36 | 248 | (Ib)-IMes | 10.8 | 15 | 8.4 MPa | 800 rpm | 138 | 3 | 1.8 |
| Ex. 7 | 36 | 248 | (Ib)-SIMes | 10.8 | 15 | 8.4 MPa | 800 rpm | 138 | 4 | 3.7 |
| Ex. 8 | 36 | 248 | (Ib)-IPr | 10.8 | 15 | 8.4 MPa | 800 rpm | 138 | 5 | 10.1 |
| Ex. 9 | 36 | 248 | (Ia)-SIMes | 10.8 | 15 | 8.4 MPa | 800 rpm | 80 | 3 | 0.6 |
| Ex. 10 | 36 | 248 | (Ia)-SIMes | 10.8 | 15 | 8.4 MPa | 800 rpm | 65 | 4 | 1.8 |
| Ex. 11 | 36 | 248 | (Ia)-SIMes | 10.8 | 15 | 8.4 MPa | 800 rpm | 50 | 23 | 0.8 |
| Ex. 12 | 36 | 248 | (Ia)-SIMes | 5.4 | 15 | 8.4 MPa | 800 rpm | 138 | 5 | 7.6 |
| Ex. 13 | 18 | 266 | (Ia)-SIMes | 10.8 | 15 | 8.4 MPa | 800 rpm | 138 | 1 | 0.4 |
| Ex. 14 | 36 | 248 | (Ia)-SIMes | 10.8 | 15 | 8.4 MPa | 800 rpm | 138 | 3 | 0.4 |
| Ex. 15 | 36 | 248 | (Ia)-SIMes | 10.8 | 15 | 8.4 MPa | 800 rpm | 138 | 3 | 1.3 |

Example 16: Hydrogenation of Nitrile Rubber Latex

A nitrile rubber with an ACN content of 38.2% by weight, $M_n$=133,668, $M_w$=529,408, and PDI=3.96 present in latex form was subjected to hydrogenation under the conditions given in the following Table 6:

TABLE 6

| Example 16 | | |
|---|---|---|
| Cat. Ru Complex (Ia)-SIMes | 36.5 mg | 0.4 phr |
| MCB solvent for catalyst | 10 ml | |
| NBR latex (6 wt %) | 152 g | |
| $H_2$ pressure | 8.4 MPa | |
| Temp. | 138° C. | |

The above mentioned NBR latex was diluted to 6 wt % solid content by adding deionized water. 152 g of the diluted NBR latex was filled into an autoclave (600 mL volume) and bubbled with nitrogen gas for 20 minutes to remove dissolved oxygen; the autoclave was heated to 138° C., and then 36.5 mg (0.4 phr) of the Catalyst (Ia)-SIMes (dissolved in 10 mL degassed MCB) solution was shot into the autoclave by hydrogen gas, and the hydrogen pressure was raised to 8.4 MPa. Samples were taken out at intervals for FT-IR test to monitor the RDB. After 19 hours, the latex was cooled down and the pressure was released. Finally the HNBR latex was coagulated by adding $CaCl_2$ and dried in vacuo.

After 19 hours, the final hydrogenation conversion reached 98%.

The invention claimed is:
1. A complex having the general formula (I)

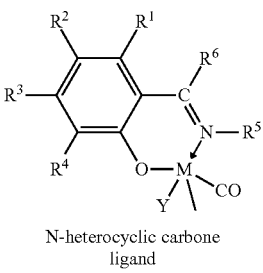

N-heterocyclic carbene ligand wherein:
  M is ruthenium or osmium;
  Y represents H, F, Cl, Br, I, $CF_3$, pyridine, —$OC_6H_5$, $CF_3COO$—, $CH_3SO_3$—, or $BF_4$;
  $R^1$, $R^2$, $R^3$, and $R^4$ are identical or different and represent
    H; $NO_2$; $CF_3$; halogen; or straight chain or branched, substituted or unsubstituted $C_1$-$C_{14}$-alkyl; or substituted or unsubstituted $C_3$-$C_{10}$-cycloalkyl; or substituted or unsubstituted $C_6$-$C_{14}$-aryl, which aryl group is either unsubstituted or contains 1, 2, 3, 4 or 5 substituents; or $OR^7$, $OC(=O)R^7$, $CO(=O)R^7$, $SO_3R^7$, $SO_3N(R^7)_2$ or $SO_3Na$ wherein $R^7$ represents H, straight chain or branched, substituted or unsubstituted $C_1$-$C_{14}$-alkyl; or $(N(R^8)_3)^+X^-$ wherein X is halide, and $R^8$ are identical or different and represent H; straight chain or branched, substituted or unsubstituted $C_1$-$C_{14}$-alkyl, substituted or unsubstituted $C_6$-$C_{14}$-aryl, which aryl group is either unsubstituted or contains 1, 2, 3, 4 or 5 substituents; or tris ($C_1$-$C_6$-alkoxy)silyl-$C_1$-$C_6$-alkyl, tris ($C_6$-$C_{14}$-aryloxy)silyl-$C_1$-$C_6$-alkyl, or tris($C_3$-$C_{10}$-cycloalkoxy)silyl-$C_1$-$C_6$-alkyl;

$R^5$ represents H; or straight chain or branched, substituted or unsubstituted $C_1$-$C_{14}$-alkyl; or substituted or unsubstituted $C_3$-$C_{10}$-cycloalkyl; or substituted or unsubstituted $C_6$-$C_{14}$-aryl, which aryl group is either unsubstituted or contains 1, 2, 3, 4 or 5 identical or different substituents; and $R^6$ represents H, or straight chain or branched, substituted or unsubstituted $C_1$-$C_{14}$-alkyl; or substituted or unsubstituted $C_3$-$C_{10}$-cycloalkyl; or substituted or unsubstituted $C_6$-$C_{14}$-aryl, which aryl group is either unsubstituted or contains 1, 2, 3, 4 or 5 substituents.

2. The complex of general formula (I) according to claim 1, wherein:

M is ruthenium;

Y is H or Cl;

$R^1$, $R^2$, $R^3$, and $R^4$ are identical or different and represent H; $NO_2$; F, Cl, or Br; or straight chain or branched, substituted or unsubstituted $C_1$-$C_8$-alkyl; or substituted or unsubstituted $C_5$-$C_8$-cycloalkyl; or substituted or unsubstituted $C_6$-$C_{14}$-aryl, which aryl group is either unsubstituted or contains 1, 2, 3, 4 or 5 identical or different substituents; or $OR^7$, $OC(=O)R^7$, $CO(=O)R^7$, $SO_3R^7$, $SO_3N(R^7)_2$ or $SO_3Na$ wherein $R^7$ represents H, straight chain or branched, substituted or unsubstituted $C_1$-$C_{14}$-alkyl;

$R^5$ represents H; or straight chain or branched, substituted or unsubstituted $C_1$-$C_{14}$-alkyl; or substituted or unsubstituted $C_3$-$C_{10}$-cycloalkyl; or substituted or unsubstituted $C_6$-$C_{14}$-aryl, which aryl group is either unsubstituted or contains 1, 2, 3, 4 or 5 identical or different substituents; and $R^6$ represents H, or straight chain or branched, substituted or unsubstituted $C_1$-$C_{14}$-alkyl; or substituted or unsubstituted $C_3$-$C_{10}$-cycloalkyl; or substituted or unsubstituted $C_6$-$C_{14}$-aryl, which aryl group is either unsubstituted or contains 1, 2, 3, 4 or 5 identical or different substituents.

3. The complex of general formula (I) according to claim 1, wherein:

M is ruthenium,

Y is H or Cl, $R^1$, $R^2$, $R^3$, and $R^4$ are all H or $R^1$, $R^3$, and $R^4$ are all H while $R^2$ is simultaneously $NO_2$;

$R^5$ represents H;

straight chain or branched, substituted or unsubstituted $C_1$-$C_8$-alkyl; or substituted or unsubstituted $C_5$-$C_8$-cycloalkyl; or substituted or unsubstituted $C_6$-$C_{10}$-aryl, which aryl group is either unsubstituted or contains 1, 2, 3, 4 or 5 identical or different substituents; and $R^6$ represents H, or straight chain or branched, substituted or unsubstituted $C_1$-$C_{14}$-alkyl; or substituted or unsubstituted $C_3$-$C_{10}$-cycloalkyl; or substituted or unsubstituted $C_6$-$C_{14}$-aryl, which aryl group is either unsubstituted or contains 1, 2, 3, 4 or 5 identical or different substituents.

4. The complex of the general formula (I) according to claim 1, wherein the N-heterocyclic carbene ligand comprises a cyclic carbene type ligand based on imidazoline or imidazolidine moieties and having at least one nitrogen as hetero atom present in the ring.

5. The complex according to claim 4, wherein, in the N-heterocyclic carbene ligand in the complex of the general formula (I), $R^6$ and $R^9$ are identical or different and represent hydrogen, $C_6$-$C_{24}$-aryl, or form a cycloalkyl or aryl structure together with the carbon atoms to which they are bound, and $R^{10}$ and $R^{11}$ are identical or different represent straight-chain or branched $C_1$-$C_{10}$-alkyl, $C_3$-$C_{10}$-cycloalkyl, substituted or unsubstituted $C_6$-$C_{24}$-aryl, 2,6-diisopropylphenyl, 2,6-dimethylphenyl, 2,4,6-trimethylphenyl, $C_1$-$C_{10}$-alkylsulfonate, or $C_6$-$C_{10}$-arylsulfonate.

6. The complex according to claim 1, wherein the N-heterocyclic carbene ligand in the complex of the general formula (I) has the structures (IIIa) to (IIIu), where "Ph" means in each case phenyl, "Bu" means in each case butyl, "Mes" represents in each case 2,4,6-trimethylphenyl, "Dipp" means in all cases 2,6-diisopropylphenyl, and "Dimp" means in each case 2,6-dimethylphenyl

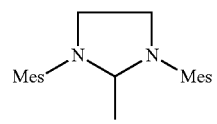
(IIIa)

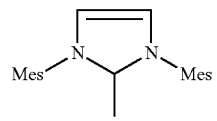
(IIIb)

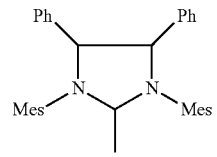
(IIIc)

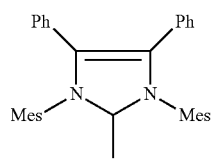
(IIId)

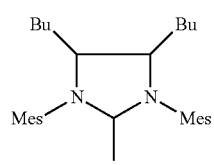
(IIIe)

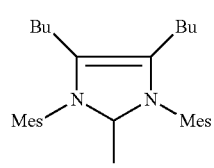
(IIIf)

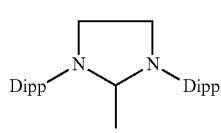
(IIIg)

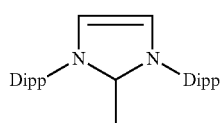
(IIIh)

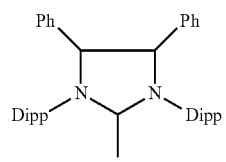
(IIIj)

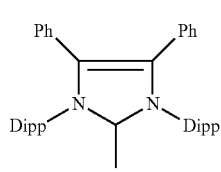
(IIIk)

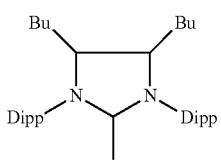
(IIIm)

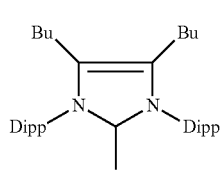
(IIIn)

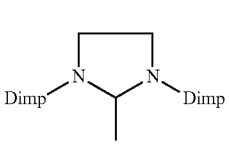
(IIIp)

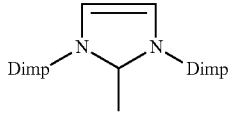
(IIIq)

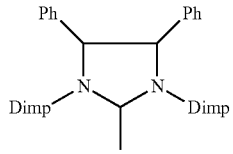
(IIIr)

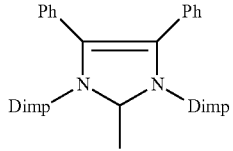
(IIIs)

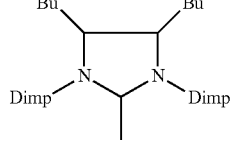
(IIIt)

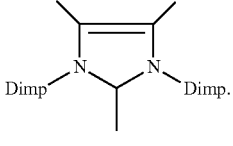
(IIIu)

7. The complex according to claim 1, wherein the complex of general formula (I) is selected from the group consisting of (Ia)-IMes, (Ia)-SIMes, (Ia)-IPr, (Ib)-IMes, (Ib)-SIMes, (Ib)-IPr, (Ic)-IMes, (Ic)-SIMes, (Ic)-IPr, wherein "IMes" means N,N'-bis(mesityl)imidazol-2-ylidene, "SIMes" means N,N'-bis(mesityl)imidazolidin-2-ylidene, "IPR" means N,N'-bis(2,6-diisopropyl-phenyl)imidazol-2-ylidene and "ItBu" means N,N'-bis(tert-butyl)imidazol-2-ylidene,

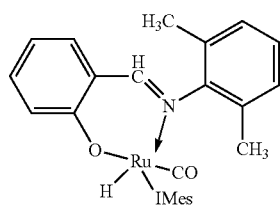
(Ia)-IMes

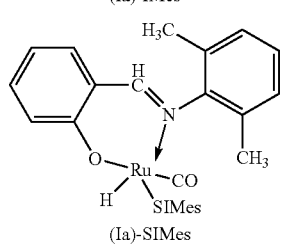
(Ia)-SIMes

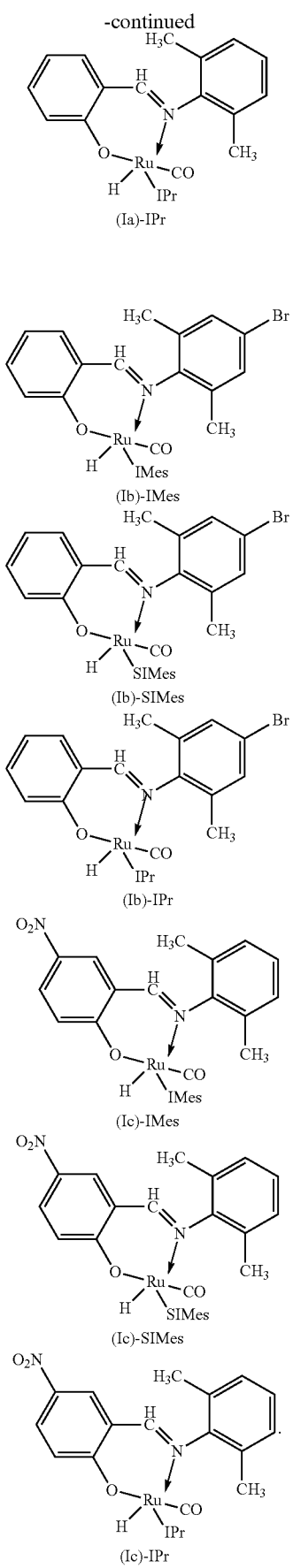

8. A process for preparing the complex of general formula (I) according to claim 1, the process comprising:
reacting a compound of general formula (1)

$$MXY(CO)(PR_3)_n \quad (1)$$

wherein:
M is ruthenium or osmium;
X is H, Cl, Br or I;
Y represents H, F, Cl, Br, I, $CF_3$, pyridine, —$OC_6H_5$, $CF_3COO$—, $CH_3SO_3$—, or $BF_4$;
R represents
substituted or unsubstituted $C_1$-$C_{14}$-alkyl;
substituted or unsubstituted $C_3$-$C_8$-cycloalkyl;
substituted or unsubstituted $C_6$-$C_{14}$-aryl; and
n is 3, if R represent substituted or unsubstituted $C_6$-$C_{14}$-aryl; or
n is 2, if R represent substituted or unsubstituted $C_1$-$C_{14}$-alkyl, or substituted or unsubstituted $C_3$-$C_8$-cycloalkyl;
with a compound of general formula (2)

(2)

wherein
$R^1$, $R^2$, $R^3$, and $R^4$ are identical or different and represent
H; $NO_2$; $CF_3$; halogen; or
straight chain or branched, substituted or unsubstituted $C_1$-$C_{14}$-alkyl;
substituted or unsubstituted $C_3$-$C_{10}$-cycloalkyl;
substituted or unsubstituted $C_6$-$C_{14}$-aryl, which aryl group is either unsubstituted or contains 1, 2, 3, 4 or 5 identical or different substituents;
$OR^7$, $OC(=O)R^7$, $CO(=O)R^7$, $SO_3R^7$, $SO_3N(R^7)_2$ or $SO_3Na$ wherein $R^7$ represents H, straight chain or branched, substituted or unsubstituted $C_1$-$C_{14}$-alkyl;
$(N(R^8)_3)^+X^-$ wherein X is halide, and $R^8$ are identical or different and represent H; straight chain or branched, substituted or unsubstituted $C_1$-$C_{14}$-alkyl, substituted or unsubstituted $C_6$-$C_{14}$-aryl, which aryl group is either unsubstituted or contains 1, 2, 3, 4 or 5 identical or different substituents; or
tris ($C_1$-$C_6$-alkoxy)silyl-$C_1$-$C_6$-alkyl, tris ($C_6$-$C_{14}$-aryloxy)silyl-$C_1$-$C_6$-alkyl, or tris($C_3$-$C_{10}$-cycloalkoxy)silyl-$C_1$-$C_6$-alkyl;
$R^5$ represents H;
straight chain or branched, substituted or unsubstituted $C_1$-$C_{14}$-alkyl;
substituted or unsubstituted $C_3$-$C_{10}$-cycloalkyl;
substituted or unsubstituted $C_6$-$C_{14}$-aryl, which aryl group is either unsubstituted or contains 1, 2, 3, 4 or 5 identical or different substituents; and R⁶ represents H, or
straight chain or branched, substituted or unsubstituted $C_1$-$C_{14}$-alkyl; or
substituted or unsubstituted $C_3$-$C_{10}$-cycloalkyl; or
substituted or unsubstituted $C_6$-$C_{14}$-aryl, which aryl group is either unsubstituted or contains 1, 2, 3, 4 or 5 identical or different substituents;
to yield a compound of general formula (3)

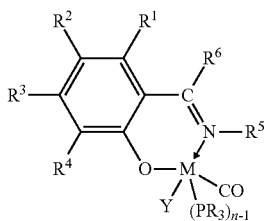

(3)

wherein
$R^1$, $R^2$, $R^3$, $R^4$, $R^5$, $R^6$, n, M, Y and R shall have the same meanings as outlined above for general formulae (1) and (2); and
reacting the compound of the general formula (3) with an N-heterocyclic carbene to yield the compounds of general formula (I).

9. The process according to claim 8, comprising:
reacting a compound of general formula (1) wherein:
M is ruthenium;
X is H, Cl, Br or I;
Y represents H, F, Cl, Br, I, $CF_3$, pyridine, —$OC_6H_5$, $CF_3COO$—, $CH_3SO_3$—, or $BF_4$, and
$PR_3$ represents either triphenyl phosphine ($PPh_3$) with n being 3 or tricyclohexyl phosphine ($PCy_3$) with n being 2,
with a compound of general formula (2) wherein:
$R^1$, $R^2$, $R^3$, and $R^4$ are identical or different and represent
H; $NO_2$; F, Cl, or Br; or
substituted or unsubstituted methyl, ethyl, n-propyl, i-propyl, n-butyl, i-butyl, and tert.-butyl;
substituted or unsubstituted cyclopentyl, cyclohexyl or cycloheptyl;
phenyl, either unsubstituted or containing 1, 2, 3, 4 or 5 substituents;
$OR^7$, $OC(=O)R^7$, $CO(=O)R^7$, $SO_3R^7$, $SO_3N(R^7)_2$ or $SO_3Na$ wherein $R^7$ represents H, substituted or unsubstituted methyl, ethyl, n-propyl, i-propyl, n-butyl, i-butyl, or tert.-butyl;
$R^5$ methyl, ethyl, n-propyl, i-propyl, n-butyl, i-butyl, and tert.-butyl which is either unsubstituted or substituted with $OR^7$, $OC(=O)R^7$, or $CO(=O)R^7$, wherein $R^7$ represents H, straight chain or branched, substituted or unsubstituted methyl, ethyl, n-propyl, i-propyl, n-butyl, i-butyl, or tert.-butyl;
phenyl, which is either unsubstituted or which contains 1, 2 or 3 identical or different substituents which are located in the o- and/or p-positions and which are selected from the group consisting of methyl, ethyl, n-propyl, i-propyl, n-butyl, i-butyl, and tert.-butyl, Cl, Br, and I, $OR^7$, $OC(=O)R^7$, or $CO(=O)R^7$ wherein $R^7$ represents H, substituted or unsubstituted methyl, ethyl, n-propyl, i-propyl, n-butyl, i-butyl, or tert.-butyl; and R⁶ represents H, or
substituted or unsubstituted methyl, ethyl, n-propyl, i-propyl, n-butyl, i-butyl, or tert.-butyl; or
substituted or unsubstituted cyclopentyl, cyclohexyl or cycloheptyl; or
phenyl, either unsubstituted or containing 1, 2, 3, 4 or 5 identical or different substituents;
to yield a compound of general formula (3) wherein:
M is ruthenium
$R^1$, $R^2$, $R^3$, $R^4$, $R^5$, $R^6$, n, Y and R shall have the same meanings as outlined above for the embodiments of general formulae (1) and (2); and
reacting the compound of the general formula (3) with the N-heterocyclic carbene to result in the compound of general formula (I) wherein M is ruthenium and $R^1$, $R^2$, $R^3$, $R^4$, $R^5$, and Y shall have the same meanings as outlined above for the compounds of general formulae (1) and (2).

10. The process according to claim 8, wherein the compound of general formula (1) is selected from the group consisting of $RuHCl(CO)(PR_3)_n$, $RuH_2(CO)(PR_3)_n$, and $RuCl_2(CO)(PR_3)_n$ and the compound of general formula (2) is selected from the group consisting of

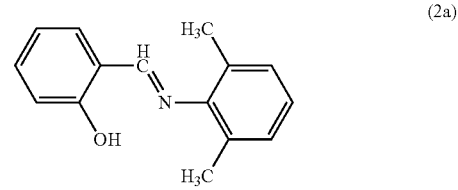

(2a)

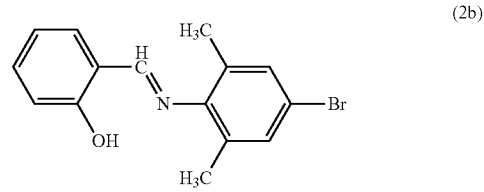

(2b)

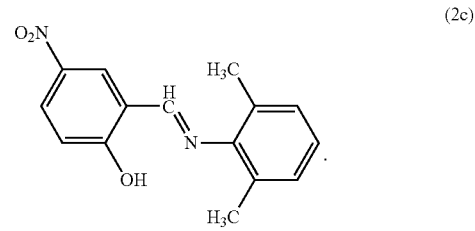

(2c)

11. The process according to claim 10, wherein the compound of general formula (3) is a compound of the following formulae

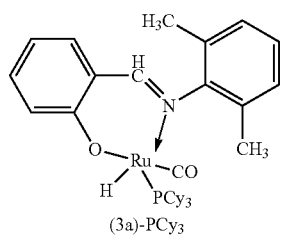

(3a)-PCy₃

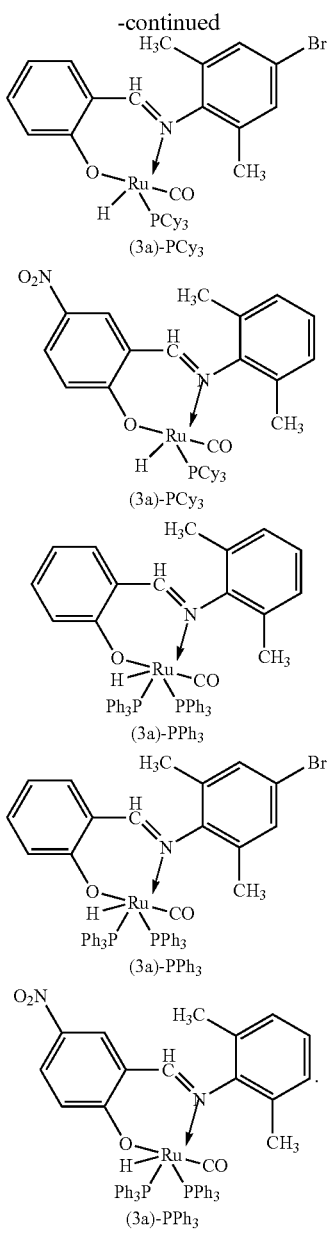

(3a)-PCy₃

(3a)-PCy₃

(3a)-PPh₃

(3a)-PPh₃

(3a)-PPh₃

12. A process for preparing the complex according to claim 1, the process comprising:

reacting a compound of general formula (4)

MXY(CO)(N-heterocyclic carbene)(PR₃)      (4)

wherein:

M is ruthenium or osmium,

X is H, Cl, Br or I;

Y represents H, F, Cl, Br, I, CF₃, pyridine, —OC₆H₅, CF₃COO—, CH₃SO₃—, or BF₄

R is identical or different, and represents substituted or unsubstituted $C_1$-$C_{14}$-alkyl; or substituted or unsubstituted $C_3$-$C_8$-cycloalkyl; or substituted or unsubstituted $C_6$-$C_{14}$-aryl; and n is 3, if R represent substituted or unsubstituted $C_6$-$C_{14}$-aryl; or n is 2, if R represent substituted or unsubstituted $C_1$-$C_{14}$-alkyl or substituted or unsubstituted $C_3$-$C_8$-cycloalkyl;

with a compound of general formula (2)

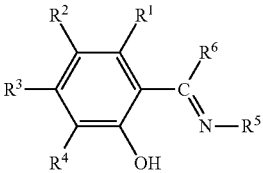

(2)

wherein:

$R^1$, $R^2$, $R^3$, and $R^4$ are identical or different and represent

H; NO₂; CF₃; halogen; or straight chain or branched, substituted or unsubstituted $C_1$-$C_{14}$-alkyl; or substituted or unsubstituted $C_3$-$C_{10}$-cycloalkyl; or substituted or unsubstituted $C_6$-$C_{14}$-aryl, which aryl group is either unsubstituted or contains 1, 2, 3, 4 or 5 substituents; or OR⁷, OC(=O)R⁷, CO(=O)R⁷, SO₃R⁷, SO₃N(R⁷)₂ or SO₃Na wherein R⁷ represents H, straight chain or branched, substituted or unsubstituted $C_1$-$C_{14}$-alkyl; or (N(R⁸)₃)⁺X⁻ wherein X is halide, and R⁸ are identical or different and represent H; straight chain or branched, substituted or unsubstituted $C_1$-$C_{14}$-alkyl, substituted or unsubstituted $C_6$-$C_{14}$-aryl, which aryl group is either unsubstituted or contains 1, 2, 3, 4 or 5 substituents; or tris ($C_1$-$C_6$-alkoxy)silyl-$C_1$-$C_6$-alkyl, tris ($C_6$-$C_{14}$-aryloxy)silyl-$C_1$-$C_6$-alkyl, or tris($C_3$-$C_{10}$-cycloalkoxy)silyl-$C_1$-$C_6$-alkyl;

R⁵ represents H;

straight chain or branched, substituted or unsubstituted $C_1$-$C_{14}$-alkyl;

substituted or unsubstituted $C_3$-$C_{10}$-cycloalkyl;

substituted or unsubstituted $C_6$-$C_{14}$-aryl, which aryl group is either unsubstituted or contains 1, 2, 3, 4 or 5 identical or different substituents; and R⁶ represents H, or straight chain or branched, substituted or unsubstituted $C_1$-$C_{14}$-alkyl; or substituted or unsubstituted $C_3$-$C_{10}$-cycloalkyl; or substituted or unsubstituted $C_6$-$C_{14}$-aryl, which aryl group is either unsubstituted or contains 1, 2, 3, 4 or 5 identical or different substituents;

to yield a compound of general formula (I) wherein R¹, R², R³, R⁴, R⁵, Y, M and R shall have the same meanings as outlined above for general formulae (2) and (4).

13. The process according to claim 12, wherein the compound of general formula (4) is selected from the group consisting of RuHCl(CO)(IMes)(PPh₃), RuHCl(CO)(SIMes)(PPh₃), RuHCl(CO)(IPr)(PPh₃), RuHCl(CO)(IMes)(PCy₃), RuHCl(CO)(SIMes)(PCy₃), and RuHCl(CO)(IPr)(PCy₃).

14. The process according to claim 8, wherein the reaction is performed in one or more organic solvents, and either without any catalyst or in the presence of at least one catalyst.

15. A method for hydrogenating compounds, the method comprising contacting the compounds with hydrogen in the presence of the complex of general formula (I) according to claim 1 as catalysts.

16. A process for manufacturing partially or fully saturated compounds, the process comprising contacting unsaturated compounds containing at least one C=C double bond, or oligomers or polymers having carbon-carbon double bonds, with hydrogen in the presence of at least one complex of general formula (I) according of claim 1.

17. The process according to claim 16, wherein the unsaturated compounds comprise a polymer comprising repeating units of (i) at least one conjugated diene, (ii) at least one α,β-unsaturated nitrile monomer, and (iii) none, one or more termonomers.

18. The process according to claim 16, wherein the hydrogenation is carried out at a temperature of 30° C. to 200° C., and at a hydrogen pressure of 0.5 MPa to 35 MPa.

19. The process according to claim 16, wherein the amount of the complex of general formula (I) to the unsaturated compounds, is 1 to 1000 ppm by weight the ruthenium and osmium, based on the unsaturated compounds.

20. The process according to claim 17, wherein:
the diene-based polymer is present in an aqueous suspension; and
the complex of general formula (I) is used in an amount of 0.01 to 5.0% by weight based on the weight of the diene-based polymer present in the aqueous suspension.

21. The complex of general formula (I) according to claim 1, wherein:
M is ruthenium or osmium;
Y represents H, F, Cl, Br, I, $CF_3$, pyridine, —$OC_6H_5$, $CF_3COO$—, $CH_3SO_3$—, or $BF_4$;
$R^1$, $R^2$, $R^3$, and $R^4$ are identical or different and represent
H; $NO_2$; $CF_3$; or halogen; or
straight chain or branched, substituted or unsubstituted $C_1$-$C_8$-alkyl; or
substituted or unsubstituted $C_5$-$C_8$-cycloalkyl; or
substituted or unsubstituted $C_6$-$C_{10}$-aryl, which aryl group is either unsubstituted or contains 1, 2, 3, 4 or 5 identical or different substituents; or
$OR^7$, $OC(=O)R^7$, $CO(=O)R^7$, $SO_3R^7$, $SO_3N(R^7)_2$ or $SO_3Na$ wherein $R^7$ represents H, straight chain or branched, substituted or unsubstituted $C_1$-$C_8$-alkyl; or
$(N(R^8)_3)^+X^-$ wherein X is halide, and $R^8$ are identical or different and represent H; straight chain or branched, substituted or unsubstituted $C_1$-$C_8$-alkyl; substituted or unsubstituted $C_6$-$C_{10}$-aryl, which aryl group is either unsubstituted or contains 1, 2, 3, 4 or 5 substituents; or
tris ($C_1$-$C_6$-alkoxy)silyl-$C_1$-$C_6$-alkyl, tris ($C_6$-$C_{14}$-aryloxy)silyl-$C_1$-$C_6$-alkyl, or tris($C_3$-$C_{10}$-cycloalkoxy)silyl-$C_1$-$C_6$-alkyl;
$R^5$ represents H; or
straight chain or branched, substituted or unsubstituted $C_1$-$C_8$-alkyl; or
substituted or unsubstituted $C_5$-$C_8$-cycloalkyl; or
substituted or unsubstituted $C_6$-$C_{10}$-aryl, which aryl group is either unsubstituted or contains 1, 2, 3, 4 or 5 identical or different substituents; and $R^6$ represents H, or
straight chain or branched, substituted or unsubstituted $C_1$-$C_8$-alkyl; or
substituted or unsubstituted $C_5$-$C_8$-cycloalkyl; or
substituted or unsubstituted $C_6$-$C_{10}$-aryl, which aryl group is either unsubstituted or contains 1, 2, 3, 4 or 5 substituents.

22. The complex of general formula (I) according to claim 21, wherein;
M is ruthenium or osmium;
Y represents H, F, Cl, Br, I, $CF_3$, pyridine, —$OC_6H_5$, $CF_3COO$—, $CH_3SO_3$—, or $BF_4$;
$R^1$, $R^2$, $R^3$, and $R^4$ are identical or different and represent
H; $NO_2$; $CF_3$; F, Cl, Br, or I; or
substituted or unsubstituted methyl, ethyl, n-propyl, i-propyl, n-butyl, i-butyl, or tert.-butyl; or
substituted or unsubstituted cyclopentyl, cyclohexyl or cycloheptyl; or
phenyl, either unsubstituted or containing 1, 2, 3, 4 or 5 identical or different substituents; or
$OR^7$, $OC(O)R^7$, $CO(=O)R^7$, $SO_3R^7$, $SO_3N(R^7)_2$ or $SO_3Na$ wherein $R^7$ represents H, substituted or unsubstituted methyl, ethyl, n-propyl, i-propyl, n-butyl, i-butyl, or tert.-butyl; or
$N(CH_3)(C_2H_5)_2^+$ $Cl^-$, $N(C_2H_5)_2H^+Cl^-$, $NH(CH_3)_2^+$ $Cl^-$, or $N(CH_3)_3^+Cl^-$; or trisethoxysilyl-n-propyl;
$R^5$ represents H; or
substituted or unsubstituted methyl, ethyl, n-propyl, i-propyl, n-butyl, i-butyl, or tert.-butyl; or
substituted or unsubstituted cyclopentyl, cyclohexyl or cycloheptyl; or
phenyl, which is either unsubstituted or contains 1, 2, or 3 identical or different substituents which are located in the o- and/or p-positions; and
$R^6$ represents H, or
substituted or unsubstituted methyl, ethyl, n-propyl, i-propyl, n-butyl, i-butyl, or tert.-butyl; or
substituted or unsubstituted cyclopentyl, cyclohexyl or cycloheptyl; or
phenyl, which is either unsubstituted or contains 1, 2, 3, 4 or 5 substituents.

23. The complex of the general formula (I) according to claim 4, wherein the N-heterocyclic carbene ligand comprises a cyclic carbene type ligand having a structure corresponding to the general formulae (IIa) to (IIe)

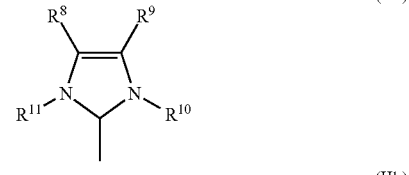
(IIa)

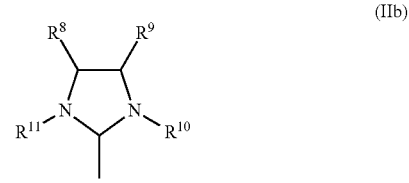
(IIb)

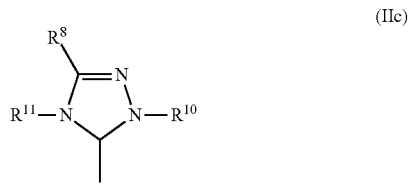
(IIc)

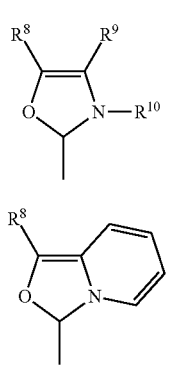

(IId)

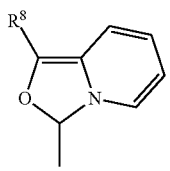

(IIe)

wherein:

R$^8$, R$^9$, R$^{10}$ and R$^{11}$ are identical or different and represent hydrogen, straight-chain or branched C$_1$-C$_{30}$-alkyl, C$_3$-C$_{20}$-cycloalkyl, C$_2$-C$_{20}$-alkenyl, C$_2$-C$_{20}$-alkynyl, C$_6$-C$_{24}$-aryl, C$_7$-C$_{25}$-alkaryl, C$_2$-C$_{20}$-heteroaryl, C$_2$-C$_{20}$-heterocyclyl, C$_1$-C$_{20}$-alkoxy, C$_2$-C$_{20}$-alkenyloxy, C$_2$-C$_{20}$-alkynyloxy, C$_6$-C$_{20}$-aryloxy, C$_2$-C$_{20}$-alkoxycarbonyl, C$_1$-C$_{20}$-alkylthio, C$_6$-C$_{20}$-arylthio, —Si(R)$_3$, —O—Si(R)$_3$, —O—C(=O)R, C(=O)R, —C(=O)N(R)$_2$, —NR—C(=O)—N(R)$_2$, —SO$_2$N(R)$_2$, —S(=O)R, —S(=O)$_2$R, —O—S(=O)$_2$R, halogen, nitro or cyano; wherein in all above occurrences relating to the meanings of R$^8$, R$^9$, R$^{10}$ and R$^{11}$ the group R is identical or different and represents hydrogen, C$_1$-C$_{30}$-alkyl, C$_3$-C$_{20}$-cycloalkyl, C$_2$-C$_{20}$-alkenyl, C$_2$-C$_{20}$-alkynyl, C$_6$-C$_{24}$-aryl, or C$_2$-C$_{20}$-heteroaryl, and wherein R$^8$, R$^9$, R$^{10}$, and R$^{11}$ can independently of one another, be unsubstituted or substituted by one or more substituents selected from the group consisting of straight-chain or branched C$_1$-C$_{10}$-alkyl, C$_3$-C$_8$-cycloalkyl, C$_1$-C$_{10}$-alkoxy, C$_6$-C$_{24}$-aryl, C$_2$-C$_{20}$-heteroaryl, C$_2$-C$_{20}$-heterocyclyl, a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen, wherein the abovementioned substituents can independently of one another be either unsubstituted or are, in turn, substituted by one or more further substituents selected from the group consisting of chlorine or bromine, C$_1$-C$_5$-alkyl, C$_1$-C$_5$-alkoxy and phenyl.

24. The complex according to claim 5, wherein, in the N-heterocyclic carbene ligand in the complex of the general formula (I), R$^8$ and R$^9$ are identical or different and represent hydrogen, phenyl, straight-chain or branched methyl, ethyl, n-propyl, i-propyl, n-butyl, sec-butyl, and i-butyl, or form a cycloalkyl or aryl structure together with the carbon atoms to which they are bound, and R$^{10}$ and R$^{11}$ are identical or different and represent i-propyl or neopentyl, adamantyl, phenyl, 2,6-diisopropylphenyl, 2,6-dimethylphenyl, 2,4,6-trimethylphenyl, C$_1$-C$_{10}$-alkylsulfonate, or C$_6$-C$_{10}$-arylsulfonate.

25. The process according to claim 8, wherein:

M is ruthenium or osmium;

X is H, Cl, Br or I;

Y represents H, F, Cl, Br, I, CF$_3$, pyridine, —OC$_6$H$_5$, CF$_3$COO—, CH$_3$SO$_3$—, or BF$_4$;

R represents straight chain or branched, substituted or unsubstituted C$_1$-C$_6$-alkyl;

substituted or unsubstituted cyclopentyl, cyclohexyl or cycloheptyl;

substituted or unsubstituted phenyl; and n is 3, if R represent substituted or unsubstituted phenyl; or n is 2, if R represent substituted or unsubstituted C$_1$-C$_6$-alkyl, or substituted or unsubstituted cyclopentyl, cyclohexyl or cycloheptyl;

R$^1$, R$^2$, R$^3$, and R$^4$ are identical or different and represent H; NO$_2$; CF$_3$; or halogen, straight chain or branched, substituted or unsubstituted C$_1$-C$_8$-alkyl, substituted or unsubstituted C$_5$-C$_8$-cycloalkyl, substituted or unsubstituted C$_6$-C$_{10}$-aryl, which aryl group is either unsubstituted or contains 1, 2, 3, 4 or 5 identical or different substituents;

OR$^7$, OC(O)R$^7$, CO(=O)R$^7$, SO$_3$R$^7$, SO$_3$N(R$^7$)$_2$ or SO$_3$Na wherein R$^7$ represents H, straight chain or branched, substituted or unsubstituted C$_1$-C$_8$-alkyl;

(N(R$^8$)$_3$)$^+$X$^-$ wherein X is chloride, and R$^8$ are identical or different and represent H; straight chain or branched, substituted or unsubstituted C$_1$-C$_8$-alkyl; substituted or unsubstituted C$_6$-C$_{10}$-aryl, which aryl group is either unsubstituted or contains 1, 2, 3, 4 or 5 identical or different substituents; or tris (C$_1$-C$_6$-alkoxy)silyl-C$_1$-C$_6$-alkyl, tris (C$_6$-C$_{14}$-aryloxy)silyl-C$_1$-C$_6$-alkyl, or tris(C$_3$-C$_{10}$-cycloalkoxy) silyl-C$_1$-C$_6$-alkyl;

R$^5$ represents H;

straight chain or branched, substituted or unsubstituted C$_1$-C$_8$-alkyl;

substituted or unsubstituted C$_5$-C$_8$-cycloalkyl; or substituted or unsubstituted C$_6$-C$_{14}$-aryl, which aryl group is either unsubstituted or contains 1, 2 or 3 identical or different substituents which are located in the o- and/or p-positions; and R$^6$ represents H, or straight chain or branched, substituted or unsubstituted C$_1$-C$_8$-alkyl; or substituted or unsubstituted C$_5$-C$_8$-cycloalkyl; or substituted or unsubstituted C$_6$-C$_{10}$-aryl, which aryl group is either unsubstituted or contains 1, 2, 3, 4 or 5 identical or different substituents.

26. The process according to claim 8, wherein the compound of general formula (1) is selected from the group consisting of RuHCl(CO)(PCy$_3$)$_2$, RuHCl(CO)(PPh$_3$)$_3$, RuCl$_2$(CO)(PCy$_3$)$_2$, RuCl$_2$(CO)(PPh$_3$)$_3$, RuH$_2$(CO)(PCy$_3$)$_2$, and RuH$_2$(CO)(PPh$_3$)$_3$ and the compound of general formula (2) is selected from the group consisting of

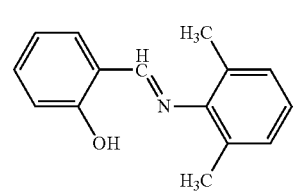

(2a)

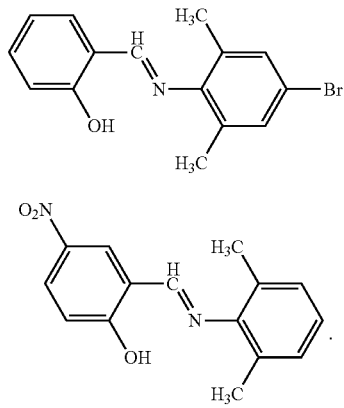

27. The process for preparing the complexes according to claim 12, wherein:
M is ruthenium,
X is H, Cl, Br or I;
Y represents H, F, Cl, Br, I, $CF_3$, pyridine, —$OC_6H_5$, $CF_3COO$—, $CH_3SO_3$—, or $BF_4$
R is identical or different and represents
substituted or unsubstituted $C_1$-$C_6$-alkyl; or
substituted or unsubstituted cyclopentyl, cyclohexyl or cycloheptyl; or
substituted or unsubstituted phenyl; and
n is 3, if the R represent substituted or unsubstituted phenyl; or
n is 2, if the R represent substituted or unsubstituted $C_1$-$C_6$-alkyl or substituted or unsubstituted cyclopentyl, cyclohexyl or cycloheptyl;
$R^1$, $R^2$, $R^3$, and $R^4$ are identical or different and represent H; $NO_2$; $CF_3$; F, Cl, Br, or I; or
substituted or unsubstituted methyl, ethyl, n-propyl, i-propyl, n-butyl, i-butyl, and tert.-butyl; or
substituted or unsubstituted cyclopentyl, cyclohexyl or cycloheptyl; or
phenyl, either unsubstituted or containing 1, 2, 3, 4 or 5 substituents; or
$OR^7$, $OC(O)R^7$, $CO(=O)R^7$, $SO_3R^7$, $SO_3N(R^7)_2$ or $SO_3Na$ wherein $R^7$ represents H, substituted or unsubstituted methyl, ethyl, n-propyl, i-propyl, n-butyl, i-butyl, or tert.-butyl; or
$(N(R^8)_3)^+X^-$ wherein X is chloride, and $R^8$ are identical or different and represent H; substituted or unsubstituted methyl, ethyl, n-propyl, i-propyl, n-butyl, i-butyl, and tert.-butyl; phenyl, either unsubstituted or containing 1, 2, 3, 4 or 5 substituents; or
tris ($C_1$-$C_6$-alkoxy)silyl-$C_1$-$C_6$-alkyl, tris ($C_6$-$C_{14}$-aryloxy)silyl-$C_1$-$C_6$-alkyl, or tris($C_3$-$C_{40}$-cycloalkoxy)silyl-$C_1$-$C_6$-alkyl;
$R^5$ represents H; or
substituted or unsubstituted methyl, ethyl, n-propyl, i-propyl, n-butyl, i-butyl, and tert.-butyl; or
substituted or unsubstituted cyclopentyl, cyclohexyl or cycloheptyl; or
phenyl, either unsubstituted or 1, 2 or 3 identical or different substituents which are located in the o- and/or p-positions; and
$R^6$ represents H, or
substituted or unsubstituted methyl, ethyl, n-propyl, i-propyl, n-butyl, i-butyl, or tert.-butyl; or
substituted or unsubstituted cyclopentyl, cyclohexyl or cycloheptyl; or
phenyl, either unsubstituted or containing 1, 2, 3, 4 or 5 identical or different substituents.

28. The process according to claim 14, wherein the organic solvent is selected from the group consisting of THF, dioxane, and diethylether, hexane, toluene and benzene, chloroform and chlorobenzene, ethyl acetate, methyl ethyl ketone, acetone, and methanol, ethanol and methyloxyethanol, and the catalyst is $Ag_2CO_3$ or TlOEt.

29. The process according to claim 16, wherein the unsaturated compounds containing at least one C=C double bond comprise terminal olefins, internal olefins, cyclic olefins, conjugated olefins, any further olefins having at least one carbon-carbon double bond and additionally at least one further polar unsaturated double or triple bond.

30. The process according to claim 29, wherein:
the unsaturated compounds comprise a nitrite rubber comprising repeat units of:
(i) at least one conjugated diene selected from the group consisting of 1,3-butadiene, isoprene, 1-methylbutadiene, 2,3-dimethylbutadiene, piperylene, or chloroprene, or mixtures thereof,
(ii) at least one α,β-unsaturated nitrite monomer selected from the group consisting of acrylonitrile, methacrylonitrile, ethacrylonitrile and mixtures thereof, and
(iii) none, one or more termonomers, selected from the group consisting of α,β-unsaturated, monocarboxylic acids, their esters and amides, α,β-unsaturated, dicarboxylic acids, their mono- or diesters, the respective anhydrides and amides of the α,β-unsaturated dicarboxylic acids;
the hydrogenation is carried out at a temperature of 50° C. to 160° C. and at a hydrogen pressure of 3.0 MPa to 10 MPa; and
the amount of the complex of general formula (I) to the nitrite rubber is 5 to 250 ppm by weight, based on the nitrile rubber.

* * * * *